(12) United States Patent
Sinderby et al.

(10) Patent No.: US 12,420,037 B2
(45) Date of Patent: Sep. 23, 2025

(54) SYSTEMS, DEVICES AND METHODS FOR MODULATING A RESPIRATORY DRIVE OF A PATIENT

(71) Applicant: UNITY HEALTH TORONTO, Toronto (CA)

(72) Inventors: Christer Sinderby, Toronto (CA); Jennifer Beck, Toronto (CA); Norman Comtois, Scarborough (CA)

(73) Assignee: UNITY HEALTH TORONTO, Toronto (CA)

( * ) Notice: Subject to any disclaimer, the term of this patent is extended or adjusted under 35 U.S.C. 154(b) by 1002 days.

(21) Appl. No.: 17/277,780

(22) PCT Filed: Sep. 19, 2019

(86) PCT No.: PCT/CA2019/051329
§ 371 (c)(1),
(2) Date: Mar. 19, 2021

(87) PCT Pub. No.: WO2020/056511
PCT Pub. Date: Mar. 26, 2020

(65) Prior Publication Data
US 2021/0346623 A1   Nov. 11, 2021

Related U.S. Application Data

(60) Provisional application No. 62/733,377, filed on Sep. 19, 2018.

(51) Int. Cl.
*A61M 16/00*   (2006.01)
*A61M 16/06*   (2006.01)

(52) U.S. Cl.
CPC .... *A61M 16/0003* (2014.02); *A61M 16/0051* (2013.01); *A61M 16/0672* (2014.02);
(Continued)

(58) Field of Classification Search
CPC ...... A61M 16/00–22; A61M 2205/502; A61M 2205/083; A61M 2205/581;
(Continued)

(56) References Cited

U.S. PATENT DOCUMENTS 3,903,869 A * 9/1975 Bancalari ............... A61H 31/02
                                                              128/202.12
5,671,752 A   9/1997 Sinderby et al.
(Continued)

FOREIGN PATENT DOCUMENTS

TW    M544941      *  7/2017
WO    2013/140229     9/2013
(Continued)

OTHER PUBLICATIONS

TW M544941 description translation (Year: 2024).*
(Continued)

*Primary Examiner* — Timothy A Stanis
*Assistant Examiner* — Kira B Daher
(74) *Attorney, Agent, or Firm* — BCF LLP

(57) ABSTRACT

A mechanical ventilation system comprises a plurality of ventilation therapy sub-systems. Each of the ventilation therapy sub-systems is adapted to assist a respiratory function of the patient. The system also comprises a detector of the respiratory drive of the patient, an operator interface receiving one or more control parameters, and a main controller. The main controller assigns a therapeutic contribution to each of the ventilation therapy sub-systems based on the respiratory drive of the patient and on the control parameters. The controller modulates the respiratory drive of a patient by controlling each of the plurality of the ventilation therapy sub-systems according to its assigned therapeutic contribution. Distinct ventilation therapy sub-systems may apply negative pressure on the abdomen of the (Continued)

patient, deliver a non-pressurizing inspiratory flow to the patient, or induce a positive pressure in the airways of the patient.

18 Claims, 17 Drawing Sheets

(52) U.S. Cl.
CPC ............... *A61M 2205/502* (2013.01); *A61M 2210/1014* (2013.01); *A61M 2230/04* (2013.01); *A61M 2230/40* (2013.01)

(58) Field of Classification Search
CPC .... A61M 2205/583; A61M 2210/1014; A61M 2230/04; A61M 2230/40; A61M 2230/065; A61M 2230/425; A61M 2230/60; A61M 2201/107; A61M 2201/1238; A61M 2201/1628; A61M 2201/5043; A61M 2201/5058; A61M 2201/5071; A61M 2016/0027; A61M 2016/0039; A61M 2202/0208; A61H 31/02; A61B 5/037; A61B 5/113; A61B 5/285; A61B 5/349; A61B 5/389; G16H 20/40; G16H 40/60
See application file for complete search history.

(56) References Cited

U.S. PATENT DOCUMENTS

| | | | |
|---|---|---|---|
| 5,820,560 A | 10/1998 | Sinderby et al. | |
| 6,962,155 B1 | 11/2005 | Sinderby | |
| 7,909,034 B2* | 3/2011 | Sinderby | A61H 31/02 128/205.12 |
| 8,720,441 B2* | 5/2014 | Sinderby | A61B 5/08 600/536 |
| 9,795,752 B2* | 10/2017 | Birnkrant | G16H 20/40 |
| 2005/0165334 A1* | 7/2005 | Lurie | A61M 16/20 601/44 |
| 2005/0211246 A1* | 9/2005 | Beck | A61M 16/024 128/204.23 |
| 2008/0000477 A1* | 1/2008 | Huster | A61B 7/04 601/149 |
| 2008/0302364 A1* | 12/2008 | Garde | A61M 16/026 128/204.23 |
| 2010/0319691 A1* | 12/2010 | Lurie | A61M 16/085 128/205.24 |
| 2014/0296728 A1* | 10/2014 | Sinderby | A61B 5/086 600/529 |
| 2015/0053201 A1* | 2/2015 | Djupesland | A61M 11/006 128/203.18 |
| 2016/0121064 A1* | 5/2016 | Rees | A61M 16/0003 128/204.23 |
| 2017/0182275 A1* | 6/2017 | O'Donnell | A61M 16/06 |
| 2018/0368762 A1* | 12/2018 | Pirtini Cetingul | A61G 11/00 |
| 2019/0015615 A1* | 1/2019 | Sinderby | A61B 5/091 |

FOREIGN PATENT DOCUMENTS

| | | | |
|---|---|---|---|
| WO | 2015095969 | 7/2015 | |
| WO | WO-2016157105 A1 * | 10/2016 | ........ A61M 16/0051 |
| WO | 2017/113017 | 7/2017 | |
| WO | 2018231128 | 12/2018 | |

OTHER PUBLICATIONS

PCT International Search Report and PCT Written Opinion for PCT International Application No. PCT/CA2019/051329 (13 pages).
Sinderby et al., "Inspiratory Muscle Unloading by Neurally Adjusted Ventilatory Assist During Maximal Inspiratory Efforts in Healthy Subjects"; Chest, vol. 131, No. 3, Mar. 1, 2007; 7 sheets.
Spahija et al., "Patient-Ventilator Interaction During Pressure Support Ventilation and Neurally Adjusted Ventilatory Assist*"; Critical Care Medicine, vol. 38, No. 2, Feb. 1, 2010; 9 sheets.

* cited by examiner

SYSTEMS, DEVICES AND METHODS FOR MODULATING A RESPIRATORY DRIVE OF A PATIENT

CROSS REFERENCE TO RELATED APPLICATIONS

This is the national phase under 35 U.S.C. § 371 of International Application No. PCT/CA2019/051329, filed on Sep. 19, 2019, which claims priority to and the benefit of U.S. Provisional Application No. 62/733,377, filed on Sep. 19, 2018, the entire disclosures of both of which are incorporated by reference herein.

TECHNICAL FIELD

The present disclosure relates to the field of ventilatory assist technologies. More specifically, the present disclosure relates to systems, devices and methods for modulating a respiratory drive of a patient.

BACKGROUND

Positive pressure mechanical ventilation to the lungs is the cornerstone treatment for life support in critically ill patients with acute respiratory failure. Despite the life saving features of positive pressure mechanical ventilation, there are considerable adverse effects associated with such treatment methods.

Conventionally, positive pressure mechanical ventilation methods frequently rely on intubation, in which assist is delivered via an endotracheal tube that is inserted into the trachea of the patient, to obtain a required efficiency of ventilation and respiratory muscle unloading. One reason for intubation is the failure of non-invasive ventilatory assist technologies that are due to patient-ventilator asynchrony and to the need for sedation to keep the patient calm. The insertion of an endotracheal tube into the trachea of the patient has several potential adverse effects, such as an increased risk of infection and pneumonia, and has been associated with increased duration of mechanical ventilation, morbidity, and mortality.

For those patients in whom there are problems to synchronize assist delivery to their own effort, increased sedation is often required to avoid the patient reacting by "fighting the ventilator". Increased sedation and excessive assist cause a suppression of diaphragm activation and is associated with inactivity-induced atrophy of the respiratory muscles, a condition known as ventilator induced diaphragm dysfunction (VIDD). The reconditioning of weak respiratory muscles can prolong weaning and time on mechanical ventilation.

Frequently, elevated arterial $CO_2$ ($PaCO_2$) and reduced pH levels in patients with acute respiratory failure stimulate both efforts to breathe and increased assist levels that, in turn, increase lung-distending pressures and tidal volumes. Excessive inspiratory volumes and lung-distending pressures are harmful to an injured lung and can result in so called ventilator induced lung injury (VILI). VILI has been associated with increased mortality. Moreover, excessive respiratory drive and work of breathing may also result in diaphragm dysfunction.

Insufficient lung-recruitment is another frequently observed complication in patients with acute respiratory failure and injured lungs. Hence, preventing deflation/partial collapse of the lung tissue is important to prevent VILI.

Currently, positive pressure ventilation technology dominates the treatment of acute respiratory failure and acute lung injury during both invasive and non-invasive ventilation. However, both invasive and non-invasive positive pressure ventilation methods increase the lung-distending trans-pulmonary pressure and volumes, and increase the risk of VILI.

A more recent development uses a high flow nasal cannula. This technique involves a continuous and constant level of "high" flow induced through both nostrils with high leakage, during both inspiration and expiration. Use of the high flow nasal cannula has been suggested to reduce work of breathing without increasing pressure in the airways. Unfortunately, the application of continuous high flow is poor in terms of efficiency and the application of continuous high flow can induce complications, for example hyperinflation of the lungs. Also, there is a lack of solutions to quantify and measure the effect of the high flow nasal cannula on respiratory drive and work of breathing.

A particularly important problem relates to prematurely born babies, who are amounting to about 15 million per year worldwide. Premature babies are vulnerable to complications that increase morbidity and mortality in the early phase of their lives, and then frequently display handicaps later in their lives. The earlier the birth, the less developed the organs. In particular, the lungs normally develop in the late stage of pregnancy, so premature babies have underdeveloped lungs and therefore need mechanical ventilation. As the underdeveloped lungs are very delicate, pressure ventilation inflating the lungs by either positive or negative pressures can be injurious.

In very premature babies, the ventilatory assist is often required for weeks. The problems with ventilation assist are numerous. If applied invasively using an endotracheal tube, the ventilation assist is efficient but increases the risk of VILI and morbidity. If applied non-invasively, the timing and amount of assist is difficult to control and titrate using pneumatic sensors. This is due to large leaks and extremely small breath volumes during the about 80 to 90 thousand breaths per 24-hour period of premature babies. Neurally synchronized proportional positive and/or negative ventilatory assist applied to both the rib cage and the abdomen, as described for example in U.S. Pat. No. 7,909,034 B2 issued on Mar. 22, 2011 to Sinderby et al., the disclosure of which being incorporated by reference herein, can provide for more gentle ventilation in the premature babies. However, the use of proportional positive and/or negative ventilatory assist may result in lung distending pressures at injurious levels.

U.S. Pat. No. 6,962,155 B1 issued on Nov. 8, 2005 to Sinderby, the disclosure of which being incorporated by reference herein, describes techniques for maintaining at a sustainable target level a respiratory drive of a patient assisted by a lung ventilator during inspiration. U.S. Pat. No. 8,720,441 B2 issued on May 13, 2014 to Sinderby, the disclosure of which being incorporated by reference herein, describes techniques for determining a patient-ventilator breath contribution index in a spontaneously breathing, mechanically ventilated patient. Despite these advances, there is currently no method available to relieve the respiratory load and reduce the work of breathing to similar low levels as observed during invasive ventilation with endotracheal intubation in a premature baby without increasing the risk of volume and/or pressure induced trauma to the respiratory system. Moreover, high pressure-assist levels frequently result in gas insufflation of the stomach and intestines which may lead to complications.

Therefore, there is a need for improvements in the field of ventilatory assist technologies that compensate for problems related to ventilator induced diaphragm dysfunction, to ventilator induced lung injury and to the poor efficiency of more recent ventilatory assist solutions.

SUMMARY

According to the present disclosure, there is provided a mechanical ventilation system for modulating a respiratory drive of a patient. The system comprises a plurality of ventilation therapy sub-systems, a detector of the respiratory drive of the patient, an operator interface and a main controller. Each of the ventilation therapy sub-systems is adapted to assist a respiratory function of the patient. The operator interface is configured to receive one or more control parameters. The main controller is operatively connected to each of the plurality of ventilation therapy sub-systems, to the detector of the respiratory drive of the patient and to the operator interface. The main controller is configured to receive the one or more control parameters from the operator interface, receive measurements from the detector of the respiratory drive of the patient, assign, based on the respiratory drive of the patient and on the one or more control parameters, a therapeutic contribution to each of the plurality of ventilation therapy sub-systems for control of the respiratory drive of the patient, and control each of the plurality of the ventilation therapy sub-systems according to its assigned therapeutic contribution.

According to the present disclosure, there is also provided a method for modulating a respiratory drive of a patient. One or more control parameters are received from an operator interface. The respiratory drive of the patient is detected. A therapeutic contribution is assigned to each of a plurality of ventilation therapy sub-systems for control of the respiratory drive of the patient based on the respiratory drive of the patient and on the one or more control parameters, each of the ventilation therapy sub-systems being adapted to assist a respiratory function of the patient. Each of the plurality of the ventilation therapy sub-systems is controlled according to its assigned therapeutic contribution.

According to the present disclosure, there is also provided a mechanical ventilation system. The system comprises a non-pressurizing inspiratory flow delivery component and a controller. The non-pressurizing inspiratory flow delivery component is adapted for being connected to airways of a patient and adapted to deliver a flow of respiratory gas toward the airways of the patient. The controller is operatively connected to the non-pressurizing inspiratory flow delivery component. The controller is adapted to cause the non-pressurizing inspiratory flow delivery component to selectively deliver the flow of the respiratory gas toward the airways the patient, the flow being delivered at a multiple of a base flow at a start of an inspiratory phase of the patient and reducing to reach the base flow before an end of the inspiratory phase of the patient, the delivery of the respiratory gas selectively continuing at or below the base flow during an expiratory phase of the patient.

According to the present disclosure, there is also provided a mechanical ventilation system. The system comprises a diaphragm unloading component and a controller. The diaphragm unloading component is adapted for mounting on the abdomen of a patient and adapted to apply a negative pressure on the abdomen of the patient. The controller is operatively connected to the diaphragm unloading component. The controller is adapted to cause the diaphragm unloading component to selectively apply the negative pressure on the abdomen of the patient during the inspiratory phase of the patient.

According to the present disclosure, there is also provided a method for modulating a respiratory drive of a patient. A non-pressurizing inspiratory flow delivery component adapted for being connected to airways of the patient is provided. A flow of respiratory gas is selectively delivered toward the airways the patient, the flow being delivered at a multiple of a base flow at a start of an inspiratory phase of the patient and being reduced to reach the base flow before an end of the inspiratory phase of the patient. The delivery of the respiratory gas selectively continues at or below the base flow during an expiratory phase of the patient.

The present disclosure further relates to a method for modulating a respiratory drive of a patient. A diaphragm unloading component adapted for mounting on the abdomen of a patient and adapted to apply a negative pressure on the abdomen of the patient is provided. The diaphragm unloading component is caused to selectively apply the negative pressure on the abdomen of the patient during the inspiratory phase of the patient The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

Figure 1:
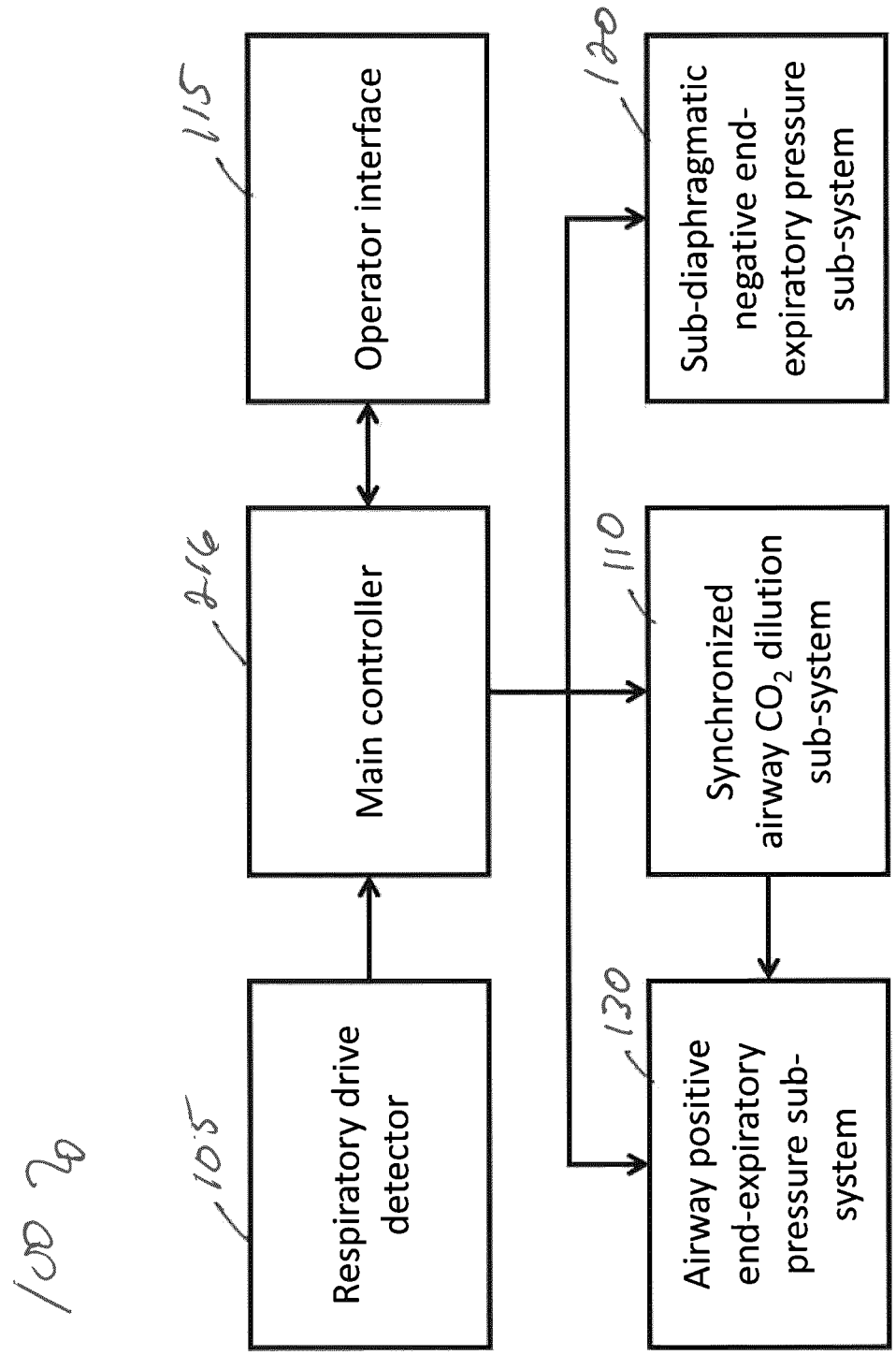
FIG. 1 is a schematic block diagram showing major components of a neural respiratory drive and volume (NRDV) modulation system for modulating a respiratory drive of a patient according to an embodiment.

Various aspects of the present disclosure generally address one or more of the problems related to ventilator induced diaphragm dysfunction, to ventilator induced lung injury and to the poor efficiency of more recent ventilatory assist solutions.

Generally stated, the present technology alleviates the shortcomings of previous solutions by introducing a non-invasive device, a non-invasive system and a non-invasive method to ensure lung-protecting unloading of respiratory muscles of critically ill patients. A mechanical ventilation system comprises a plurality of ventilation therapy sub-systems. Each of the ventilation therapy sub-systems is adapted to assist a respiratory function of the patient. A detector continuously monitors the respiratory drive of the patient. An operator interface allows a medical practitioner to supply one or more control parameters, including for example a maximum desired value for the respiratory drive of the patient. A main controller uses these control parameters and the monitored respiratory drive of the patient to calculate a therapeutic contribution that is then assigned to each of the ventilation therapy sub-systems. At any given time, one or more of the ventilation therapy sub-systems may be used to modulate the respiratory drive of the patient. The controller modulates the respiratory drive of a patient by controlling each of the plurality of the ventilation therapy sub-systems according to its assigned therapeutic contribution. Distinct ventilation therapy sub-systems may apply negative pressure on the abdomen of the patient, deliver a non-pressurizing inspiratory flow to the patient, or induce a positive pressure in the airways of the patient.

Some aspects of the present technology include:
- A reduction of respiratory drive, lung inflating pressures and breath volumes by neurally synchronized flow assist;
- Provision of specific sub-diaphragmatic unloading of the diaphragm and other inspiratory muscles without increasing lung-distending pressure and inspiratory volume and without affecting hemodynamics;
- Promotion of spontaneous breathing with adequate respiratory drive levels, thus conditioning the respiratory muscles; and
- Close loop control of neural respiratory drive by respiratory and hemodynamic reflexes to achieve effective unloading and reduction of respiratory drive, protecting the patient against ventilator induced lung injury (VILI) and ventilator induced diaphragm dysfunction (VIDD).

The present technology uses detection of neural respiratory drive and of lung reflexes. It integrates one or more of:

- A first ventilation therapy sub-system to apply synchronized airway $CO_2$ dilution ($AwCO_2Dil$) used to reduce respiratory drive and tidal volume;
- A second ventilation therapy sub-system to apply mechanical unloading by synchronized sub-diaphragmatic unloading ($Di_{SUB}UL$) to unload the inspiratory muscles by overcoming mechanical loads using synchronized sub-diaphragmatic negative pressure assist specifically directed to the abdomen of the patient to prevent an increase of lung distending pressure and volumes; and
- A third ventilation therapy sub-system to apply mechanical unloading by synchronized positive pressure assist and airway $CO_2$ dilution ($AwPass\&CO_2Dil$) to generate positive pressure in the airways of the patient, to unload respiratory muscles and reduce respiratory drive by taking advantage of excess flow administered by the synchronized airway $CO_2$ dilution ($AwCO_2Dil$).
- In some embodiments, these ventilation therapy sub-systems may support test stages used for periodically evaluating their performance.

The present technology therefore introduces an improved reflex-based monitoring and control system that favors a reduced $CO_2$ induced respiratory drive and favors diaphragm unloading and adequate ventilation without increasing the lung distending pressure and inspiratory volume of a patient. The system allows to maintain or reduce a patient's respiratory drive, driving pressures and volumes, primarily using non-invasive breathing interfaces.

Overview of a Neural Respiratory Drive and Volume (NRDV) Modulation System

Referring now to the drawings, FIG. 1 is a schematic block diagram showing major components of a neural respiratory drive and volume (NRDV) modulation system for modulating a respiratory drive of a patient according to an embodiment. The system 100 comprises a plurality of ventilation therapy sub-systems, each of which implements corresponding functions to assist a corresponding reduction of the respiratory drive of the patient. In the embodiment of FIG. 1, these sub-systems include a synchronized airway $CO_2$ dilution ($AwCO_2Dil$) sub-system 110, a synchronized sub-diaphragmatic unloading ($Di_{SUB}UL$) and sub-diaphragmatic negative end-expiratory pressure ($Di_{SUB}NEEP$) sub-system 120, and a synchronized positive pressure assist and airway $CO_2$ dilution ($AwPass\&CO_2Dil$) and airway positive end-expiratory pressure (AWPEEP) sub-system 130, all of which are operatively connected to a main controller 216. The main controller 216 may include one or more processors coupled to one or more memory devices.

The sub-system 110 uses a non-pressurizing inspiratory flow delivery component adapted for being connected to airways of the patient to selectively deliver a flow of respiratory gas toward the airways the patient. The flow is delivered at a multiple of a base flow at a start of an inspiratory phase of the patient and is reduced to reach the base flow before an end of the inspiratory phase of the patient. The delivery of the respiratory gas selectively continues at or below the base flow during an expiratory phase of the patient. The main controller 216 adjusts the multiple of the base flow according to the respective therapeutic contribution for the sub-system 110.

The sub-system 120 selectively induces a positive pressure in the airways of the patient. The main controller adjusts a level of the positive pressure according to the respective therapeutic contribution for the sub-system 120.

The sub-system 130 selectively applies a negative pressure on the abdomen of the patient during an inspiratory phase of the patient. The main controller 216 adjusts a level of the negative pressure on the abdomen of the patient according to the respective therapeutic contribution for the sub-system 130.

The sub-systems 110, 120 and 130 are described in further details hereinbelow. Use of other ventilation therapy sub-systems known in the art as a part of the system 100 is also contemplated.

The system 100 also comprises a respiratory drive detector 105 that provides measurements of a respiratory drive of a patient to the main controller 216. An operator interface 115 that may include a display, a keyboard, a mouse, a touch-sensitive screen, a microphone, a loudspeaker, and like ancillary components, allows a medical practitioner to enter one or more control parameters for use by the main controller 216.

In operation, the main controller 216 receives the one or more control parameters from the operator interface 115 and receives measurements from the respiratory drive detector 105. Using the control parameters and the respiratory drive measurements, the main controller 216 assigns a therapeutic contribution to each of the sub-systems 110, 120 and 130, in view of controlling of the respiratory drive of the patient. In an embodiment, one of the control parameters may include a maximum respiratory drive value defined for the patient by the medical practitioner, in which case each of the therapeutic contributions represents a share of an excess of the respiratory drive of the patient above the maximum respiratory drive value to be controlled by a respective one of the sub-systems 110, 120 and 130. In the same or another embodiment, one of the control parameters may include initial values for the therapeutic contributions. A 100% contribution may initially be assigned to one of the sub-systems 110, 120 or 130 if the medical practitioner desires to initially apply a single therapeutic function to the patient.

The sub-systems 110, 120 and 130 may be assigned their respective therapeutic contributions so that the sum of the therapeutic contributions is equal to 100%.

The main controller 216 controls each of the plurality of the ventilation therapy sub-systems 110, 120 and 130 according to its assigned therapeutic contribution. To this end, the main controller 216 may compare a peak of the respiratory drive of the patient (FIG. 3) with the maximum respiratory drive value defined on the operator interface 115. The main controller 216 may modify one of more of the therapeutic contributions for the sub-systems 110, 120 and/or 130 if the peak of the respiratory drive of the patient exceeds the maximum respiratory drive value. Optionally, the main controller 216 may initiate an internal timer (not shown) when setting the therapeutic contributions assigned to the sub-systems 110, 120 and 130 and then trigger an alarm, visible on the operator interface 115, if the peak of the respiratory drive of the patient still exceeds the maximum respiratory drive value upon expiry of the timer.

Figure 2:
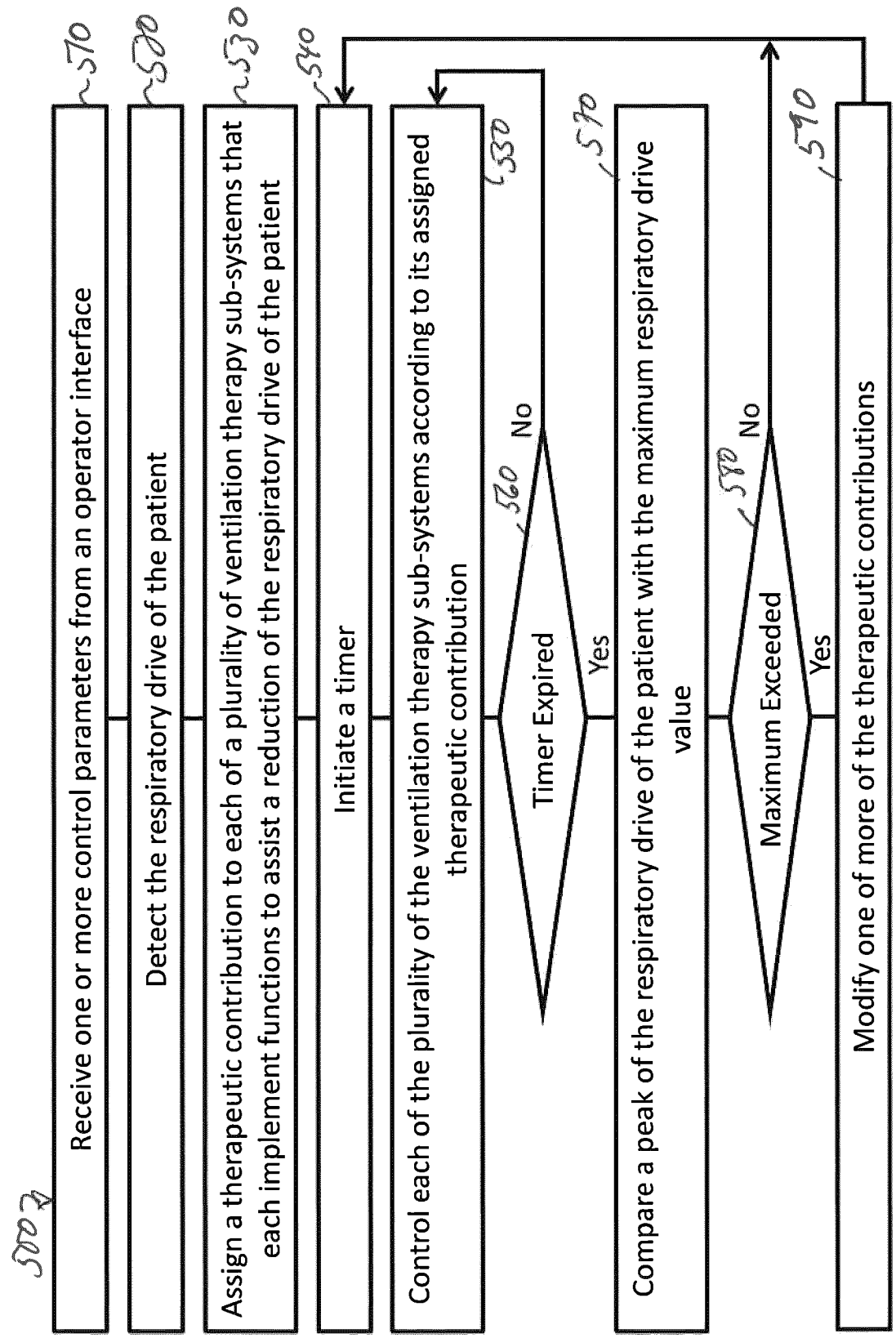
FIG. 2 is a sequence diagram showing operations of a method for modulating a respiratory drive of a patient according to an embodiment.

FIG. 2 is a sequence diagram showing operations of a method for modulating a respiratory drive of a patient according to an embodiment. On FIG. 2, a sequence 500 comprises a plurality of operations performed by the system 100, some of which may be executed in variable order, some of the operations possibly being executed concurrently, some of the operations being optional. At operation 510, the main controller 216 receives one or more control parameters from the operator interface 115. It may be noted that operation 510 may be executed from time to time as the medical practitioner may desire to modify some of the control parameters. The respiratory drive detector 115 detects the respiratory drive of the patient at operation 520.

This operation may be performed on a continuous basis or at regular intervals. At operation 530, the main controller 216 assigns, based on the respiratory drive of the patient and on the one or more control parameters, a therapeutic contribution to each of the ventilation therapy sub-systems 110, 120 and 130 that each implement corresponding functions to assist a corresponding reduction of the respiratory drive of the patient. As mentioned earlier, the therapeutic contribution assign to each of the sub-systems 110, 120 and 120 may vary between 0 and 100%, a total of the therapeutic contributions being equal to 100%. In a non-limiting example, the one or more control parameters may include a maximum respiratory drive value. In the same or another non-limiting example, each of the therapeutic contributions represents a share of an excess of the respiratory drive of the patient above a maximum respiratory drive value to be controlled by a respective one of the plurality of ventilation therapy sub-systems.

The main controller 216 may initiate a timer at operation 540, when the therapeutic contributions have been assigned to each of the plurality of ventilation therapy sub-systems. The main controller 216 controls each of the plurality of the ventilation therapy sub-systems according to its assigned therapeutic contribution at operation 550. Operation 550 may be performed on a continuous basis. Operation 560 verifies the timer. If the timer has not expired, the sequence continues with operation 550. When operation 560 determines that the timer has expired, the main controller 216 compares a peak of the respiratory drive of the patient with the maximum respiratory drive value at operation 570. At operation 580, the main controller 216 determines whether the maximum value is exceeded. If the maximum value of the respiratory drive is not exceeded, the sequence returns to operation 540 where the timer is initiated again, followed by operation 550 where the main controller 216 controls again each of the plurality of the ventilation therapy sub-systems according to its assigned therapeutic contribution at operation 550. If the maximum value is exceeded, the main controller 216 may modify one of more of the therapeutic contributions, for example to introduce one of the sub-systems 110, 120 or 130 by changing its therapeutic contribution from 0% to a value greater than 0% while, at the same time, reducing the therapeutic contribution of at least another one of the sub-systems 110, 120 or 130 so that the sum of the therapeutic contributions remains at 100%.

Other operations may be included. For example, if the main controller 216 detects that the maximum value of the respiratory drive is consistently exceeded, it may cause the operator interface 115 to issue a visual and/or audible alarm.

In some embodiments, the main controller 216 may not be configured to modify any one of the therapeutic contributions at operation 590 and may rely on the issuance of an alarm on the operator interface to modify the therapeutic conditions for the patient.

In other embodiments, the main controller 216 may be adapted to modify, or not, the therapeutic contributions at operation 590, depending on a setting of a control parameter allowing, or not, automatic setting of the therapeutic conditions.

Respiratory Drive Detection

The system 100 introduced in the description of FIG. 1 uses measurements of the respiratory drive of the patient to assign therapeutic contributions to various therapeutic sub-systems and to monitor the performance of these therapeutic sub-systems.

Figure 3:
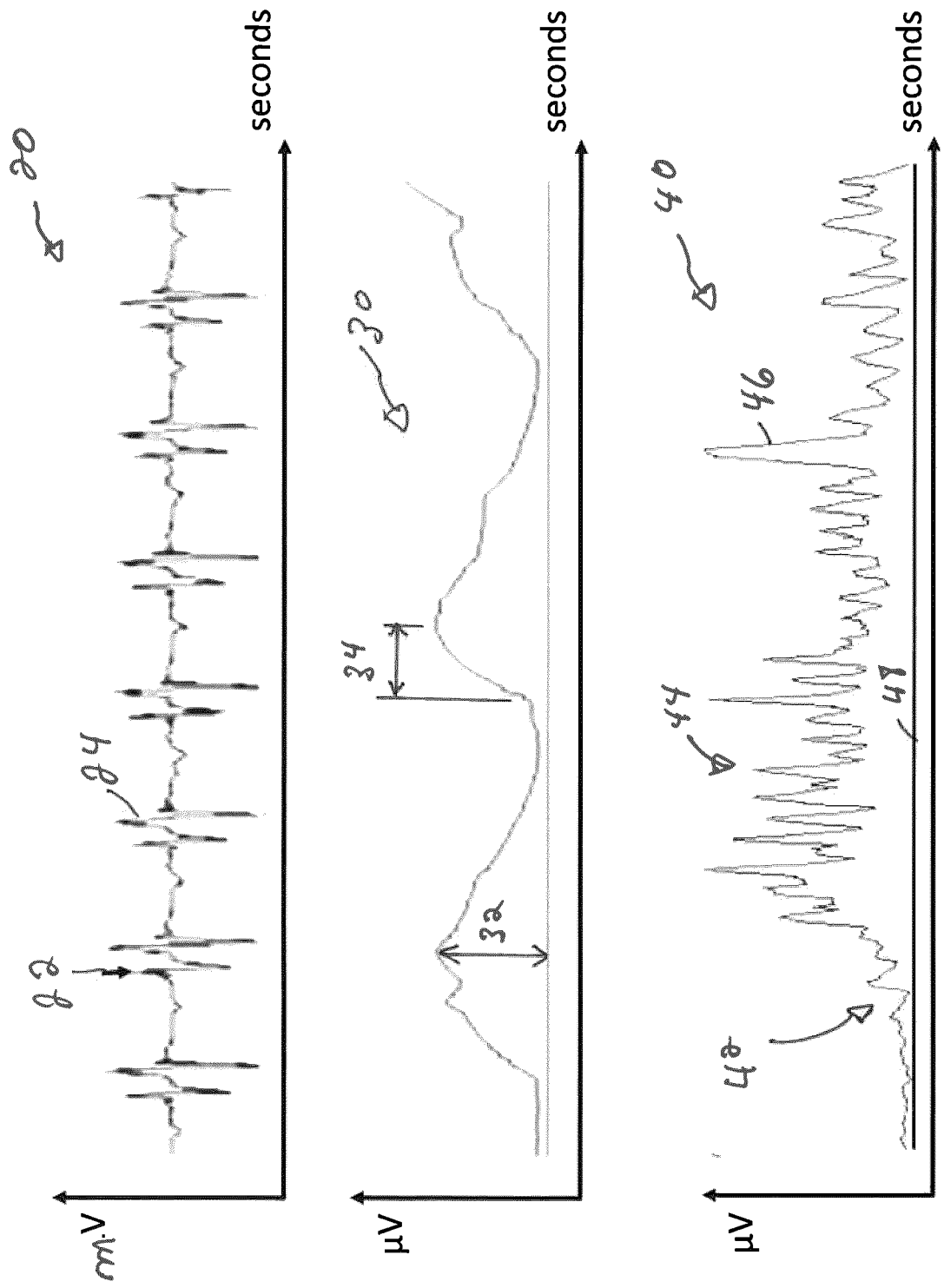
FIG. 3 shows tracings of electrical activity of the heart and of the diaphragm of a patient.

FIG. 3 shows tracings of electrical activity of the heart and of the diaphragm of a patient. Respiratory centers of a patient output electrical signals that are transmitted via the phrenic nerves to the diaphragm and whose conduction over the diaphragm may be measured as diaphragm electrical activity (EAdi). On FIG. 3, a first trace 20 depicts the electrical activity of the heart measured with an esophageal electrode, as a voltage in millivolts (mV) over time in seconds. The trace 20 highlights a P-wave 22 and a QRS-wave 24 of the heart. A second trace 30 depicts an electrical activity of the diaphragm, in microvolts (µV) over time in seconds, which is also measured using the esophageal electrode. The trace 30 highlights a peak 32 of the EAdi, as well as a rise time 34 of the EAdi ($EAdi_{T\_UP}$) that corresponds to an inspiratory phase of a breath of the patient. A third trace 40, also expressed in µV over time in seconds, provides an example of an expansion of the trace 30 over several breaths of the patient. In a first part 42 of the trace 40, the patient is in a neural apnea phase and the EAdi activity is minimal. In a following part 44 of the trace 40, the patient is breathing normally and the EAdi follows a normal curve similar to that shown on the trace 30, except for a brief sigh 46. A tonic EAdi 48 shows a lowest value of the EAdi between breaths over the entire trace 40 and thus represents a baseline of the diaphragm activity.

Figure 4:
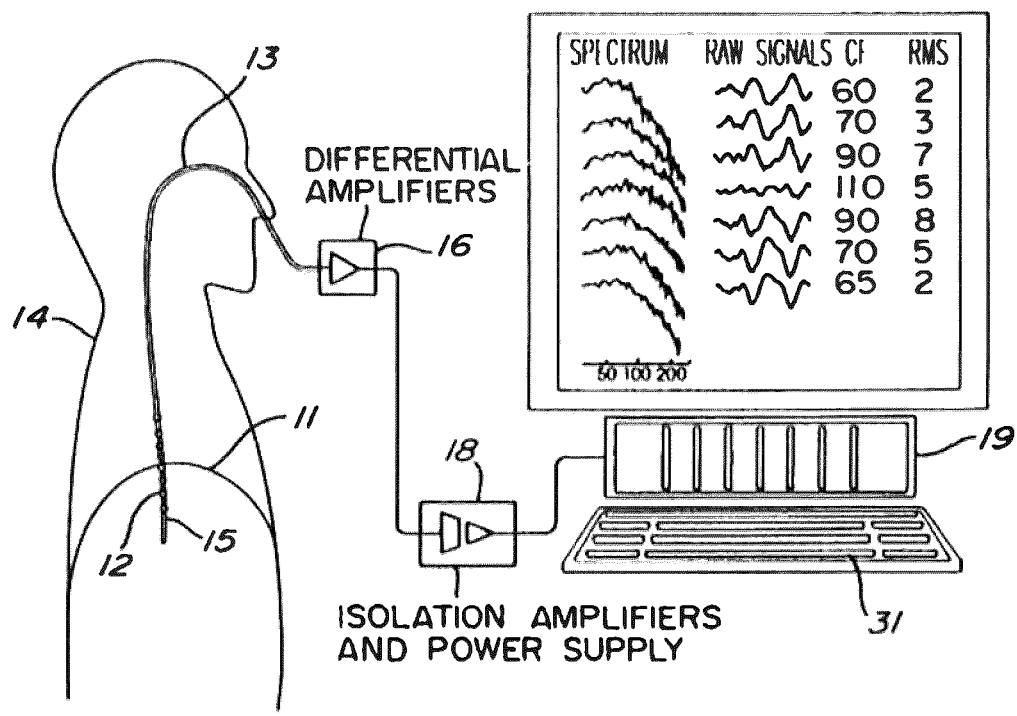
FIG. 4 is a schematic representation of a set-up of an electromyographic analysis system.
Figure 5:
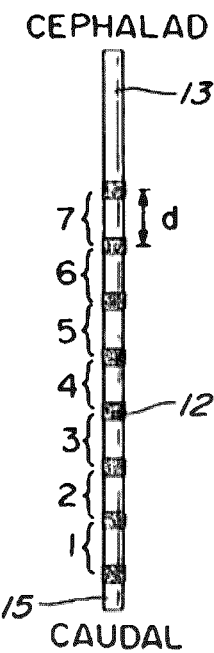
FIG. 5 is a section of oesophageal catheter on which an array of electrodes of the electromyographic analysis system of FIG. 4 is mounted.

FIG. 1 introduces the respiratory drive detector 105. Various techniques are known to measure the respiratory drive of the patient. An embodiment of the present technology uses one example of such techniques as described in U.S. Pat. No. 5,820,560 issued on Oct. 13, 1998 to Sinderby et al., the disclosure of which being incorporated by reference herein. According to this patent, the electrical activity of the heart and the EAdi may be measured using an array of electrodes mounted on an esophageal catheter passing through the center of the patient's diaphragm depolarizing region. FIG. 4 is a schematic representation of a set-up of an electromyographic analysis system. FIG. 5 is a section of oesophageal catheter on which an array of electrodes of the electromyographic analysis system of FIG. 4 is mounted. Referring at once to FIGS. 4 and 5, to measure the activity of the diaphragm 11 (EAdi) of a human patient 14, an array of electrodes such as 12 (FIGS. 4 and 5) is mounted on the free end section 15 of an oesophageal catheter 13, with a constant inter-electrode distance d (FIG. 5). As shown in FIG. 4, the catheter 13 is introduced into the patient's oesophagus through one nostril or the mouth until the array of electrodes 12 are situated at the level of the gastroesophageal junction. The diaphragm 11 and/or the oesophagus slightly move during breathing of the patient 14 whereby the array of electrodes 12 also slightly moves about the diaphragm 11.

To mount an electrode 12 on the free end section 15 of the catheter 13, stainless steel wire (not shown) may be wound around the catheter 13. The wound stainless steel wire presents a rough surface smoothed out by solder, which in turn is electroplated with nickel, copper and then gold or silver. Of course, other constructions of electrodes may be implemented.

Electric wires (not shown) interconnect each pair of successive electrodes such as 1-7 (FIG. 5) with a respective one of a group of differential amplifiers 16. Obviously, these electric wires follow the catheter 13 from the respective electrodes 12 to the corresponding amplifiers 16, and are preferably integrated to the catheter 13. Preferably, the electric wires transmitting the EAdi signals collected by the various pairs 1-7 of electrodes 12 are shielded to reduce the influence of external noise, in particular disturbance from the 50 or 60 Hz current and voltage of the electrical mains.

The group of differential amplifiers 16 amplifies (first subtraction step of a double subtraction technique, described for example in U.S. Pat. No. 5,671,752 issued on Sep. 30, 1997 to Sinderby et al., the disclosure of which being incorporated by reference herein) and band-pass filters each EAdi signal. This first subtraction step may also be carried out in a computer 19 when the amplifiers 16 are single-ended or equivalently designed amplifiers (monopolar readings). Use of other filtering techniques is also contemplated.

In the example illustrated in FIGS. 4 and 5, the free end section 15 of the catheter 13 is provided with an array of eight electrodes 12 defining seven pairs 1, 2, 3, 4, 5, 6 and 7 of successive electrodes 12 respectively collecting seven different EAdi signals. Although it has been found that activity of the diaphragm (EAdi) may be measured accurately with an oesophageal catheter 13 provided on the free end section 15 thereof with an array of eight electrodes 12, a different number and/or configuration of pairs of electrodes 12 may be contemplated depending on the patient's anatomy and movement of the diaphragm. Also, the pairs 1-7 do not need to be pairs of successive electrodes.

Signals from the esophageal catheter may be amplified, filtered, and processed. The position of the center of the patient's diaphragm depolarizing region is determined through detection of a reversal of polarity of the electromyographic component of the electrode-detected diaphragm electrical activity. First and second diaphragm electrical activity signals detected by the electrodes of the array on opposite sides of the patient's diaphragm depolarizing region are subtracted from each other, this subtraction cancelling the noise components of the first and second diaphragm electrical activity signals while adding the respective components of these first and second signals together produces a signal for EAdi having an improved signal-to-noise ratio, having a reduced electrode-position-induced filter effect.

The EAdi output signal is modulated by afferent inputs to the brain from mechano-receptors and irritant-receptors in the lungs, upper airways, respiratory muscles, as well as chemo-receptors in the aorta and brain. Reflex responses for changes in inspiratory loads, volumes or assist may be detected on a breath-to-breath basis.

The unprocessed EAdi signal measured at the gastro-esophageal junction also contain electrical signals generated by the heart. Hence the heart rate and time interval between e.g. R-R waves may be measured for each consecutive heart beat. Measuring the time interval between R-R waves is just one of possible techniques that may be used to measure the heart activity of a patient. In the context of the present disclosure, any mention of R-R interval may be substituted with a mention of heart rate; likewise, any mention of a decrease of the R-R interval is to be understood as synonymous with an increase of the heart rate. The present technology is not dependent on any particular technique for measuring a heart rate or an R-R interval.

Premature babies need parenteral feeding and are frequently provided with nasogastric feeding tubes. In an embodiment, an esophageal catheter may be incorporated in a feeding tube to measure the electrical activity of various muscles. The esophageal catheter may thus be used for recording EAdi, neural inspiratory and expiratory time, and as neural breathing frequency. Electrical signals detected by the esophageal catheter also reflect the heart activity, providing parameters such as heart rate and waveform intervals. Spectral analysis of the electrical signals may reveal early signs of muscle fatigue, for example fatigue of the diaphragm of the baby.

It is within the scope of the present disclosure to use electrical activity of a respiratory muscle other than the patient's diaphragm, or a physiological signal similar to the EAdi. Other techniques that may be used in the system 100 to detect a respiratory drive of a patient include the use of electrode implants, sensors of phrenic nerve signals, sensors of electrical activity of upper airway muscles, sensors of nose wings movements, and the like. Consequently, the following description of neural phase detection and of use of neural phase measurements is made with reference to EAdi values that may be substituted with other measurements of the respiratory drive of a patient.

Neural Phase Detection

As a part of the respiratory drive detection, neural phase detection is designed to determine turn-points of the direction in the EAdi amplitude, which are indicative of inspiratory and expiratory phases. The sensitivity of this detection is controlled by filtering the processed EAdi signal. For example, processed EAdi amplitudes for a given time unit may be filtered, for example, by a recursive filter where increasing the weight of the last EAdi sample makes the signal faster to respond whereas decreasing the weight of the last sample makes the signal slower to respond. Phase detection is thus adjusted to provide a stable direction in view of determining whether the signal is increasing or decreasing or, otherwise stated, to determine whether neural inspiration or neural exhalation is occurring at any given time.

Premature infants are characterized by strong respiratory reflexes that sometimes cause airway occlusion, either at onset of inspiration or at onset of expiration. This may be detected by observing prolonged neural inspiratory or expiratory times. As the respiratory rate is higher in newborn/pediatric patients than in adult patients, the EAdi signal response time may be adjusted to the respiratory rate. Faster responding recursive filters that place more weight on the last EAdi signal sample may thus be applied for newborns with high respiratory rate, whereas a somewhat slower responding filter suits better for adults. In a non limiting example, a recursively filtered EAdi signal placing a 10% weight on the last sample may be used for continuous proportional negative pressure unloading over the abdomen and a recursive filter placing a 7% weight on the last sample may be used for inspiratory synchronized flow in the nostril in an adult patient. In another non-limiting example, for a premature baby, a recursively filtered EAdi signal placing a 13% weight on the last sample may be used for continuous proportional negative pressure unloading over the abdomen and a 9% weight on the last sample may be used for inspiratory synchronized flow in the nostril in of the premature baby.

Figure 6:
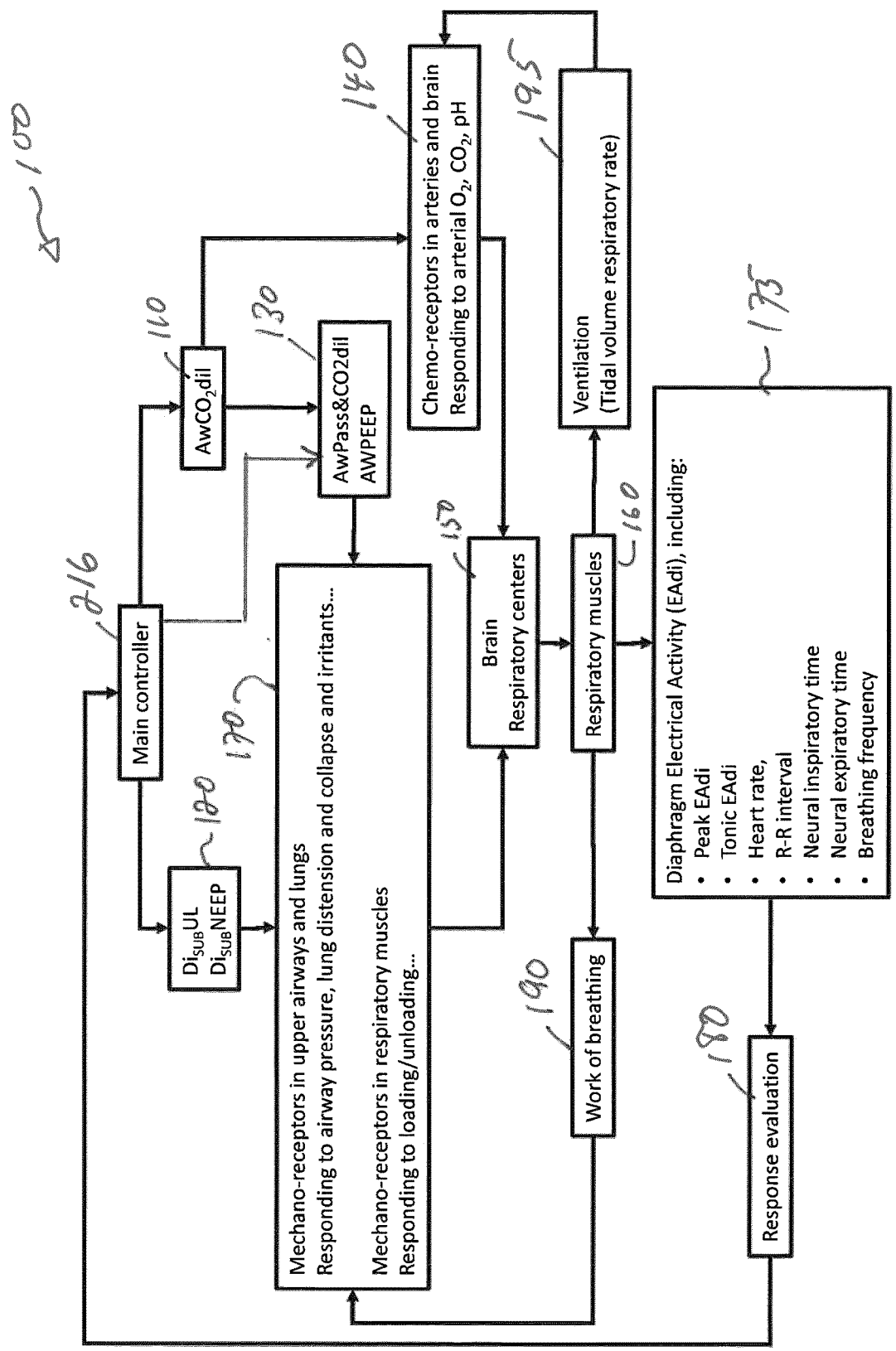
FIG. 6 is a block diagram showing the NRDV modulation system and its physiological integration according to an embodiment.

Physiological Integration of the Neural Respiratory Drive and Volume (NRDV) Modulation System FIG. 6 is a block diagram showing the NRDV modulation system and its physiological integration according to an embodiment. FIG. 6 provides a general description of how of a NRDV modulation system 100 interacts with a patient's physiological neural receptors and how diaphragm electrical signals (EAdi) are integrated.

The NRDV modulation system 100 comprises one or more main building blocks that include a synchronized airway $CO_2$ dilution (AwCO$_2$Dil) sub-system 110, a synchronized sub-diaphragmatic unloading (Di$_{SUB}$UL) and sub-diaphragmatic negative end-expiratory pressure (Di$_{SUB}$-NEEP) sub-system 120, and a synchronized positive pressure assist and airway $CO_2$ dilution (AwPass&CO$_2$Dil) and airway positive end-expiratory pressure (AWPEEP) sub-system 130.

The sub-systems 110, 120 and 130 are synchronized in that their operation is adapted to follow neural inspiratory and expiratory phases of the patient, using the EAdi signal. It should be noted that some embodiments of the present technology may include some but not all of the sub-systems 110, 120 and 130.

Parameter values input to the NRDV modulation system 100 may include:

A maximum respiratory drive value, for comparison with peak EAdi amplitudes of the patient; this maximum respiratory drive is defined as a peak EAdi limit, with values above and below the peak EAdi limit that form a hysteresis;

A tonic EAdi Upper Limit;

A peak EAdi time out limit;

A tonic EAdi time out limit;

A therapeutic contribution assignable to each of the sub-systems 110, 120 and 130, expressed as relative contribution of change in peak EAdi (EAdi change contribution) to be targeted by each of the sub-systems 110, 120 and 130;

A respiratory flow to be applied by the synchronized airway $CO_2$ dilution sub-system 110;

A negative pressure level to be applied by the synchronized sub-diaphragmatic unloading and sub-diaphragmatic negative end-expiratory pressure sub-system 120, or a negative gain for multiplying the EAdi to obtain the negative pressure level;

A positive pressure level to be applied by the synchronized positive pressure assist and airway $CO_2$ dilution and airway positive end-expiratory pressure sub-system 130, or a positive gain for multiplying the EAdi to obtain the positive pressure level; and A respiratory drive rise time increase limit applicable to an increase of EAdi rise-time (EAdi$_{T\text{-}UP}$) and a limit for the decrease of the R-R interval (i.e. limit for the increase of the heart rate), these limits being for example defined in terms of percentages.

The NRDV modulation system 100 attempts to control the peak EAdi and the tonic EAdi of the patient by controlling the sub-systems 110, 120 and/or 130. To this end, the NRDV modulation system 100 attempts to cause each of the sub-systems 110, 120 and/or 130 to modify the peak EAdi according to their respective EAdi change contributions. The peak EAdi of the patient may either be too high or too low, in which case the NRDV modulation system 100 controls the sub-systems 110, 120 and/or 130 in an attempt to return the peak EAdi of the patient to the peak EAdi limit, within bounds defined by the hysteresis. The tonic EAdi of the patient may be too high, in which case the NRDV modulation system 100 controls the sub-systems 120 and/or 130 in an attempt to reduce the tonic EAdi of the patient. When successful in reaching the peak EAdi limit and the tonic EAdi upper limit, the NRDV modulation system 100 monitors the EAdi signal of the patient to verify that these values remain within the set limits, considering the hysteresis value above and below the peak EAdi limit. If one of the peak EAdi or tonic EAdi wanders beyond the set limits, the NRDV modulation system 100 starts a timer and, if the respective time out limit is expired, the NRDV modulation system 100 once again controls the sub-systems 110, 120 and/or 130 to return the EAdi of the patient to the set values.

The synchronized AwCO$_2$Dil sub-system 110 adjusts the respiratory flow delivered toward the patient until it reaches its EAdi change contribution to the reduction of the peak EAdi or until the limit for the increase of EAdi rise-time ($EAdi_{T\text{-}UP}$) is reached. An excessive EAdi rise-time is an indication that the patient is not sufficiently ventilated. If the EAdi change contribution is met or if the $EAdi_{T\text{-}UP}$ is reached, the NRDV modulation system 100 may invoke the sub-systems 120 or 130 or both to meet the peak EAdi limit. It should be observed that the respiratory flow is delivered at an interface to the patient that does not pressurize the airways of the patient. Any portion of the respiratory flow may be inhaled by the patient and another portion of the respiratory flow may be leaked to the atmosphere. The respiratory flow is therefore delivered in the direction of (i.e. toward) the patient but is not forced in any way into the patient's airways.

The synchronized $Di_{SUB}UL$ and $Di_{SUB}NEEP$ sub-system 120 adjusts the magnitude of the negative pressure applied on the abdomen of the patient until it reaches its EAdi change contribution to the reduction of the peak EAdi or until the limit for the decrease of the R-R interval is reached. An excessive heart rate under conditions of negative abdomen pressure is an indication that a blood pressure of the patient is falling. If the EAdi change contribution is met or if the limit for the decrease of the R-R interval is reached is reached, the NRDV modulation system 100 may invoke the sub-system 130 to meet the peak EAdi limit.

The synchronized positive pressure assist and airway $CO_2$ dilution and airway positive end-expiratory pressure sub-system 130 adjusts the positive pressure applied on the airways of the patient until it reaches its EAdi change contribution to the reduction of the peak EAdi or until the limit for the increase of the R-R interval is reached, following which the NRDV modulation system 100 may invoke again the sub-system 110 and/or 120 to meet the peak EAdi limit if the peak EAdi of the patient still exceeds the peak EAdi limit. Alternatively, the NRDV modulation system 100 may cause to display a message visible to a practitioner of the system 100, for example providing a warning message, an alarm, or requesting the entry of new parameter values on a monitor.

It will be noted that the order of invocation of the sub-systems 110, 120 and 130 may differ from the above-described sequence.

The sub-system 110 mainly acts upon the chemo-receptors 140 in the arteries of the patient by favoring a $CO_2$ dilution in the airways of the patient, causing a response in the brain respiratory centers 150 that, in turn, impacts the respiratory muscles 160, including the diaphragm. The sub-systems 120 and 130 are designed to impact the mechano-receptors 170 in the upper airways and lungs of the patient to cause a response in the brain respiratory centers 150 to also impact the respiratory muscles 160. These impacts on the respiratory muscles 160 are evaluated in various manners. Firstly, the EAdi is impacted and various parameters 175 such as the peak EAdi, the tonic EAdi, the heart rate, the R-R internal, neural inspiratory and expiratory times and breathing frequency may be detected. An ongoing response evaluation 180 of the parameters 175 may be performed to close a loop of the NRDV modulation system 100, whereby the various sub-systems 110, 120 and 130 may be adjusted. The impacts of the respiratory muscles 160 also affect the work of breathing 190 that is related to the mechano-receptors 170, and the overall ventilation, expressed in tidal volume respiratory rate 195 that is calculated to estimate the impact of the chemo-receptors 140. More details on each of the sub-systems 110, 120 and 130 are provided in later descriptions of additional Figures.

Figure 7:
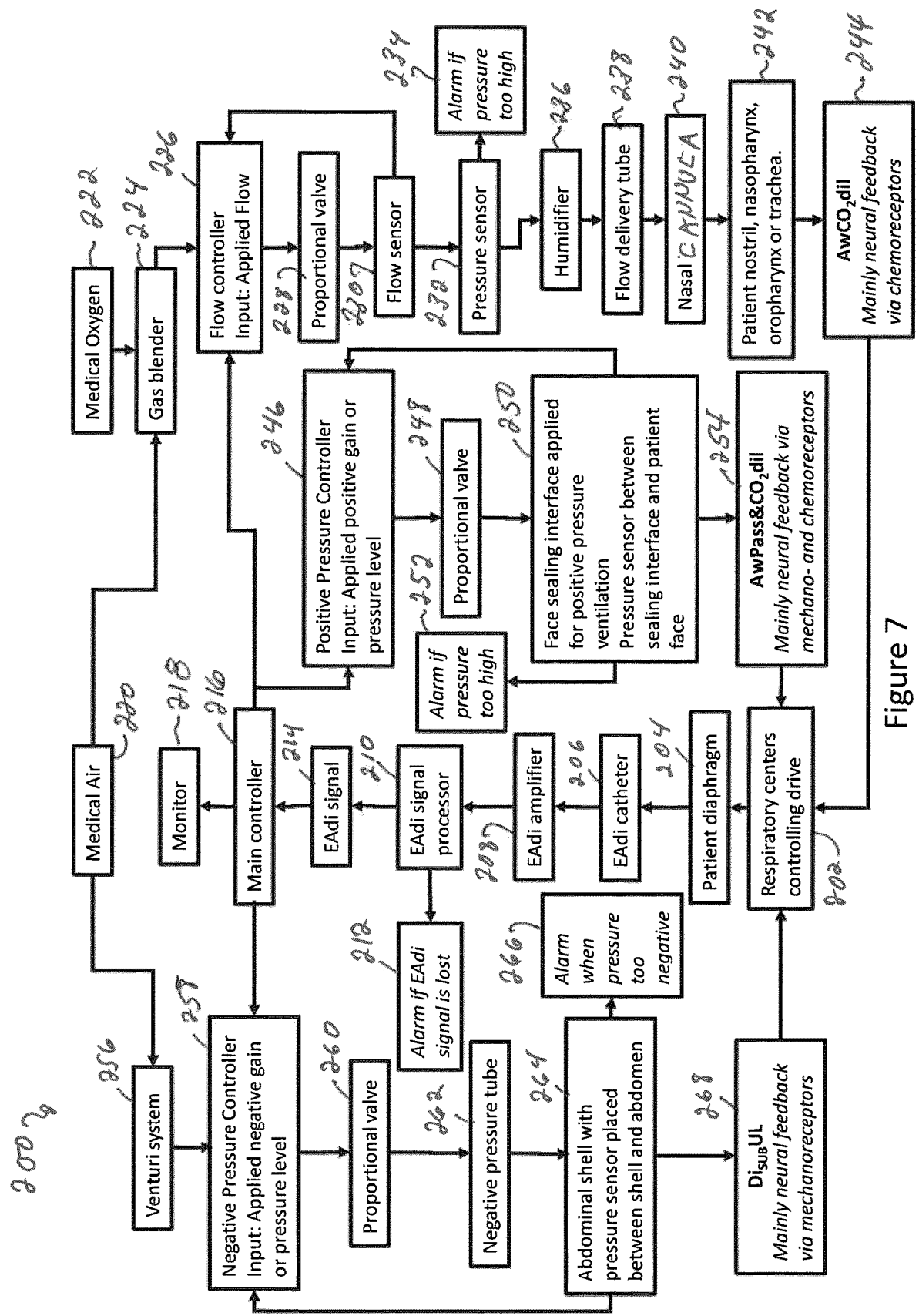
FIG. 7 is a functional view of the NRDV modulation system of FIG. 6 according to an embodiment.

Detailed Functional Description of the Neural Respiratory Drive and Volume (NRDV) Modulation System FIG. 7 is a functional view of the NRDV modulation system of FIG. 6 according to an embodiment. The various items shown on FIG. 7 may represent components of the NRDV modulation system 100, actions taken by the system 100, actions taken by a practitioner using the system 100 acting on information provided by the system 100, physical reactions of the patient, and the like.

A description of a functional view 200 of the system 100 may begin with the respiratory centers 202 of the patient, in which a neural drive controls the patient's diaphragm 204. In an embodiment, the respiratory drive detector 105 comprises an electrical diaphragm activity (EAdi) catheter 206 that provides a reading of an EAdi signal to an EAdi amplifier 208 and further to an EAdi signal processor 210. An alarm 212 may be emitted if the EAdi signal is lost by the EAdi signal processor 210. Otherwise, the EAdi signal 214 is applied to a main controller 216 for the NRDV modulation system 100. A monitor 218 may display tracings of the EAdi signal 214 and may further display operational parameters of the NRDV modulation system 100, for example the above mentioned parameter values.

Figure 8:
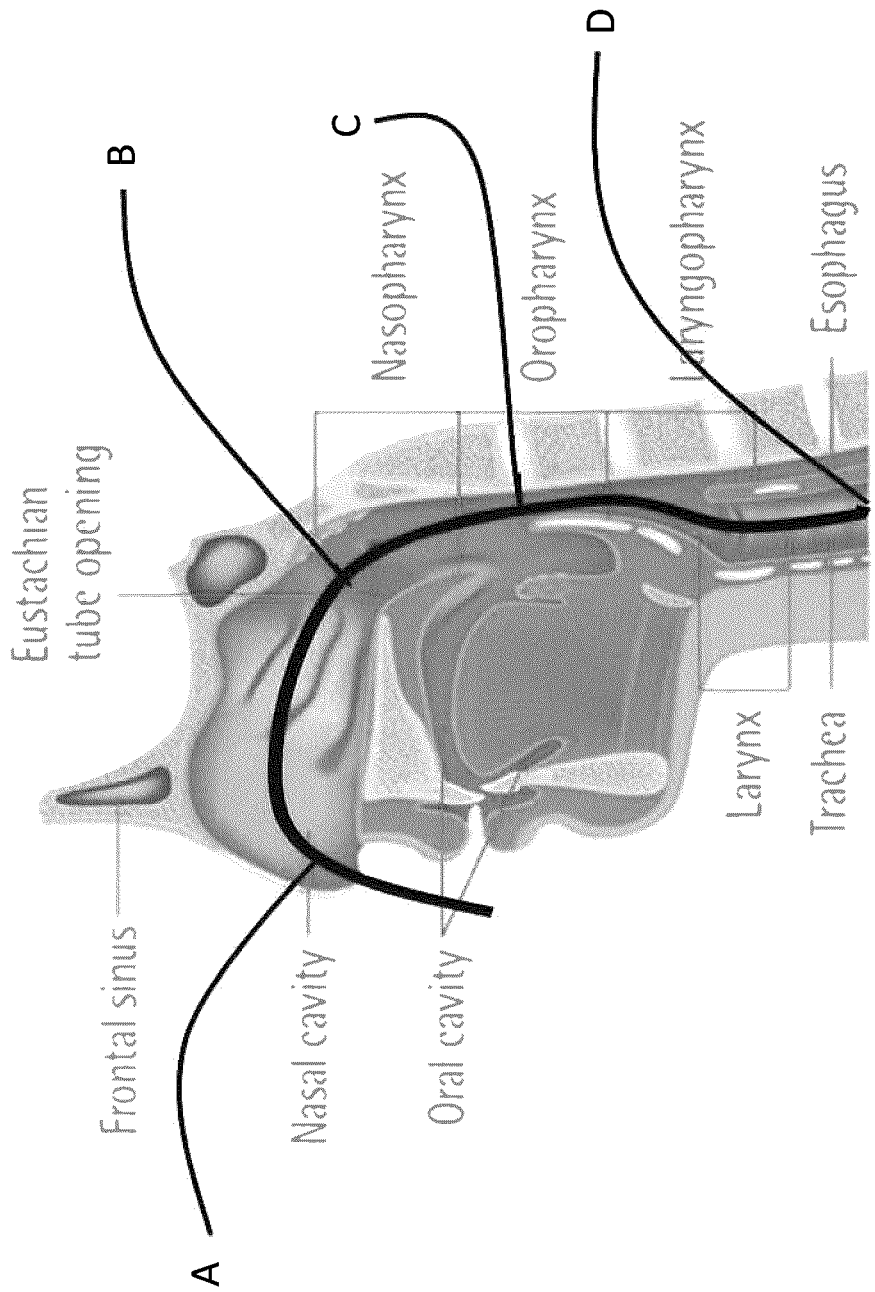
FIG. 8 shows example positions of an inspiratory flow sub-system in the airways of a patient.

The synchronized airway $CO_2$ dilution ($AwCO_2Dil$) sub-system 110 of the NRDV modulation system 100 uses a source of medical air 220 that is usually readily available in hospitals. Medical oxygen 222 may be added in a blender 224 to the medical air 220 for delivery a flow of respiratory gas to the patient, with a correct fraction of inspiratory oxygen, under the control of a flow controller 226, which is a local controller for the sub-system 110, under the general control of the main controller 216. A proportional valve 228 and a flow sensor 230 are connected to the flow controller 226 to ensure that the flow of respiratory gas is according to parameters set by the main controller 216 for the flow controller 226. A pressure sensor 232 causes the triggering of an alarm 234, which may be shown on the monitor 218, if the pressure of the flow of respiratory gas exceeds a predetermined limit. The respiratory gas may be humidified by a humidifier 236. The respiratory gas flows through an external flow delivery tube 238 connected to a non-pressurizing inspiratory flow delivery component, for example a nasal cannula 240. A non-pressurizing inspiratory flow delivery component is adapted for being connected to the airways 242 of the patient. As illustrated on FIG. 8, example positions of an inspiratory flow component in the airways of a patient comprise placing the component at the nostril (A), in the nasopharynx (B), in the oropharinx (C), or in the trachea (D). For example, the nasal cannula 240 may be mounted to one or both nostrils of the patient. The non-pressurizing inspiratory flow delivery component may have a leaky connection to the airways of the patient so that the flow of respiratory gas is delivered without pressuring the airways of the patient.

Returning to FIG. 7, the flow controller 226 tracks the EAdi signal 214 and synchronizes the flow of the respiratory gas with the neural drive of the patient. In this way, the NRDV modulation system 100 implements a dilution of $CO_2$ in the airways of the patient ($AwCO_2dil$) 244 by providing a respiratory flow that is synchronized with inspiratory phases of the patient. The patient's chemoreceptors detect this $CO_2$ dilution that, in turn, impacts respiratory centers 202 of the patient whose respiratory drive normally decreases. In an embodiment, the elements 226 to 244 of FIG. 7 generally correspond to the synchronized airway $CO_2$ dilution sub-system 110 of FIG. 6.

The practitioner may desire to add positive pressure to the airways of the patient in addition to the use of the nasal cannula 240. This is achieved by applying a face mask to the patient, the face mask causing a restriction of the expiratory flow from the patient, thereby causing a positive end expiratory pressure (PEEP) to be present in the airways of the patient. A positive pressure controller 246 under the general control of the main controller 216 determines a value for this positive pressure by applying a gain on a peak value of the EAdi signal 214. The positive pressure controller 246 controls the positive pressure by use of a proportional valve 248. The face mask being applied to the patient at 250, a pressure of the airways the patient is measured by a pressure sensor that may for example be integrated in the face mask. The pressure sensor of the face mask causes the triggering of an alarm 252, which may be shown on the monitor 218, if the pressure of the flow of respiratory gas exceeds a predetermined limit. This measurement is fed back to the positive pressure controller 246 so that a level of the positive pressure applied in the airways of the patient is controlled. In this way, the NRDV modulation system 100 implements a positive pressure assist and Airway $CO_2$ dilution (AwPASS&$CO_2$dil) 254 that is controlled by the neural respiratory drive of the patient. The patient's mechanoreceptors and chemoreceptors detect these effects that, in turn, impact respiratory centers 202 of the patient whose respiratory drive normally decreases. In an embodiment, the elements 246 to 254 of FIG. 7 generally correspond to the synchronized positive pressure assist and airway $CO_2$ dilution and airway positive end-expiratory pressure sub-system 130 of FIG. 6.

The practitioner may desire to use the synchronized sub-diaphragmatic unloading ($Di_{SUB}UL$) and sub-diaphragmatic negative end-expiratory pressure ($Di_{SUB}NEEP$) sub-system 120 to apply a negative pressure on the abdomen of the patient. A venturi system 256 is connected to the source of medical air 220 to generate the negative pressure. Other sources for negative pressure, for example a turbine or a hospital vacuum system may also be used. A negative pressure controller 258, which is a local controller for the sub-system 120, under the general control of the main controller 216 calculates a negative pressure by applying another gain to the peak value of the EAdi signal 214. The negative pressure controller 258 controls the negative pressure by use of a proportional valve 260 and applies the negative pressure via a negative pressure tube 262 on a diaphragm unloading component 264. The diaphragm unloading component 264 comprises an abdominal shell connected to a pressure sensor (not shown) and is adapted for being placed on the abdomen of the patient. A pressure reading from the pressure sensor is fed back to the negative pressure controller 258. An alarm 266 may be triggered if a magnitude of the negative pressure in the abdominal shell exceeds a predetermined threshold. In this way, the NRDV modulation system 100 implements a sub-diaphragmatic unloading ($Di_{SUB}UL$) 268 that is synchronized with inspiratory phases of the patient. The patient's mechanoreceptors detect these effects that, in turn, impact respiratory centers 202 of the patient whose respiratory drive normally decreases. In an embodiment, the elements 256 to 268 of FIG. 7 generally correspond to the sub-diaphragmatic unloading and sub-diaphragmatic negative end-expiratory pressure sub-system 120 of FIG. 6.

Considering FIGS. 6 and 7, airway $CO_2$ dilution sub-diaphragmatic unloading may operate independently or together, whereas positive pressure assist and airway $CO_2$ dilution operates jointly with synchronized airway $CO_2$ dilution. Airway $CO_2$ dilution mainly affects chemo-receptors responding to arterial $O_2$, $CO_2$, and pH. Sub-diaphragmatic unloading and positive pressure assist and airway $CO_2$ dilution mainly affect mechano-receptors in airways, lungs and respiratory muscles. Feedback from neuro-receptors affects brain and respiratory centers that, in turn, modulate the neural output to respiratory muscles, modulating the work of breathing and ventilation. The electrical signal EAdi of the diaphragm in turn provides information both to directly monitor the effect of the NRDV modulation system 100.

Neural Control of Airway $CO_2$ Dilution

An embodiment of the synchronized airway $CO_2$ dilution (AwCO$_2$Dil) sub-system 110 will now be presented in details. Conventionally, high flow therapy has only been available with constant flows set by the practitioner, due to the difficulty to precisely detect breathing efforts in high leak set ups such as high flow therapy. The airway $CO_2$ dilution method is based on a delivery of flow at higher than the normal inspiratory flow rate generated by the patient. Using measurements of the respiratory drive of the patient, the flow delivery starts at early neural inspiration without causing an increase of pressure in the airways. This is achieved by a flow delivery with high leaks. Consequently, the pressure in the airways is not reflected by the pressure of the external flow delivery tube 238. Given that volumes cannot be measured from flow and that lung-distending pressures cannot be measured via the flow circuit, neural reflexes of the patient as determined based on EAdi signals are therefore used. This is particularly useful since oxygen consumption, and cost for oxygen, may be greatly reduced given that a large part of the flow is synchronized with the inspiration.

Figure 9:
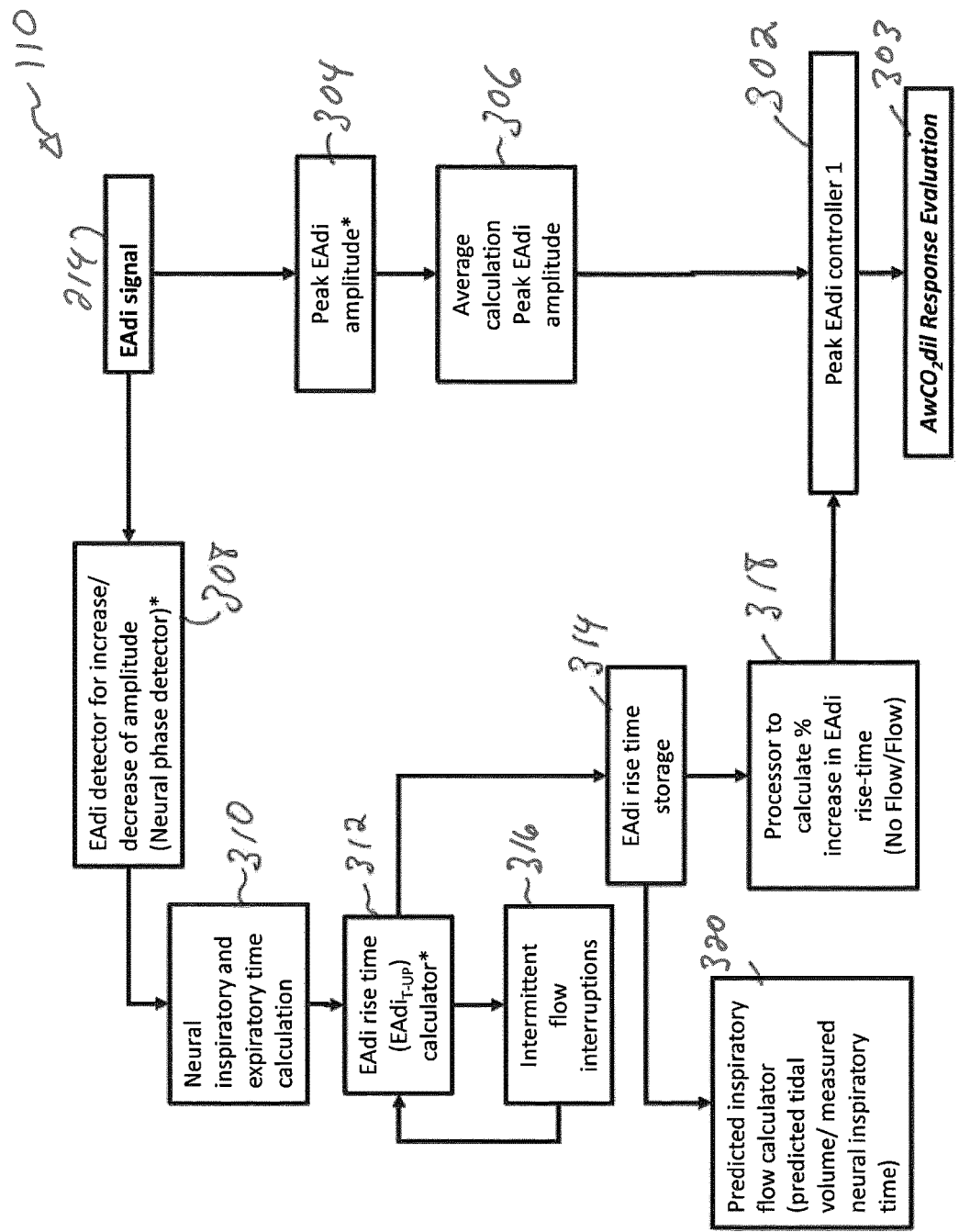
FIG. 9 is a block diagram of a synchronized airway $CO_2$ dilution sub-system according to an embodiment.

FIG. 9 is a block diagram of a synchronized airway $CO_2$ dilution sub-system according to an embodiment. FIG. 9 outlines closed loop neural feedback and reflex methods and systems used to control or guide adjustments for the airway $CO_2$ dilution. In the AwCO$_2$Dil sub-system 110, a first peak EAdi controller 302 is used to adjust a flow during airway $CO_2$ dilution. If the peak EAdi of the patient is greater than the peak EAdi limit, flow may be increased. If the peak EAdi is less than the peak EAdi limit, the flow may be reduced.

The EAdi signal 214 is fed to a peak EAdi amplitude detector 304 and may be further fed to a calculator 306 of an average peak EAdi amplitude. In any case, the peak EAdi (whether instantaneous or averaged) is provided to the first peak EAdi controller 302.

The AwCO$_2$Dil sub-system 110 also implements a neural phase detector 308. Neural inspiratory and expiratory times are calculated 310 based on the EAdi signal 214. A calculator 312 obtains an EAdi rise time ($EAdi_{T-UP}$), which is stored in a memory 314 of the first peak EAdi controller 302. Intermittent pauses 316 in the delivery of the flow of respiratory gas are performed, for example for a duration of a few breaths once every few minutes, and the calculator 312 detects a new value of the EAdi rise time. The EAdi rise time is expected to increase or remain stable during these pauses. A calculator 318 calculates an increase of the EAdi rise time, expressed for example in the form of a percentage increase, and provides this increase value to the first peak EAdi controller 302. The first peak EAdi controller 302 produces an evaluation 303 of the synchronized airway $CO_2$ dilution. EAdi rise time values are also provided by the memory 314 to a processor 320 that calculates a base inspiratory flow based on a predicted tidal volume and on the neural inspiratory time.

Generally speaking, the first peak EAdi controller 302 operates as follows. In a normal stage, it causes the delivery of the flow of the respiratory gas to the patient. From time to time, it may perform a test stage designed to evaluate a performance of the therapy. In the test stage, the delivery of the flow of the respiratory gas is momentarily paused. The EAdi rise time is expected to increase or remain stable during this pause, when compared with the EAdi rise time when the respiratory flow is normally delivered. The first peak EAdi controller 302 therefore implements a loop in which the calculator 312 and the intermittent pauses 316 cycle between normal and test stages. The loop may be terminated or parameters of the normal stage may be modified as follows. The inspiratory flow is delivered at a multiple of the base flow at the start of each inspiratory phase. The multiple of the base flow is increased and the normal stage continues if the peak of the EAdi is greater than the peak EAdi limit and the increase of the EAdi rise time is less than the respiratory drive rise time increase limit. The multiple of the base flow is decreased and the normal stage continues if the peak EAdi is less than the peak EAdi limit. The loop terminates if the increase of the EAdi rise time exceeds the respiratory drive rise time increase limit or if the peak EAdi is in a range defined between the peak EAdi limit minus the hysteresis value and the peak EAdi limit plus the hysteresis value.

If an EAdi change contribution of less than 100% has been targeted for the $AwCO_2Dil$ sub-system 110, in which case either or both of the synchronized sub-diaphragmatic unloading ($Di_{SUB}UL$) and sub-diaphragmatic negative end-expiratory pressure ($Di_{SUB}NEEP$) sub-system 120 and the synchronized positive pressure assist and airway $CO_2$ dilution ($AwPass\&CO_2Dil$) and airway positive end-expiratory pressure (AWPEEP) sub-system 130 also come into action, the first peak controller 302 determines an initial peak of the EAdi when receiving the EAdi change contribution and calculates an intermediate peak EAdi target based on the initial peak of the EAdi, on the peak EAdi limit and on the EAdi change contribution. Also, in view of the EAdi change contribution being less than 100%, the above conditions are modified as follows. The multiple of the base flow is increased if (i) the peak of the EAdi is greater than the peak EAdi limit, (ii) the peak EAdi is greater than the intermediate peak EAdi target, and (iii) the increase of the EAdi rise time is less than the respiratory drive rise time increase limit. The loop is terminated if the peak EAdi is less than the intermediate peak EAdi target. The multiple of the base flow is decreased if (i) the peak EAdi is less than the peak EAdi limit and (ii) the peak EAdi is less than the intermediate peak EAdi target. The loop is terminated if (i) the peak EAdi is less than the peak EAdi limit and (ii) the peak EAdi is greater than the intermediate peak EAdi target. The loop is also terminated if the rise time of the increase of the EAdi rise time exceeds the respiratory drive rise time increase limit. Finally, the loop is terminated if the peak EAdi is in a range defined between the peak EAdi limit minus the hysteresis value and the peak EAdi limit plus the hysteresis value. It is noted that, in an embodiment, the loop may be implemented on the basis of alarms and prompts provided on the operator interface 115 to assist a medical practitioner with suggestions to increase or decrease the multiple of the base flow when the peak EAdi is greater or smaller than the peak EAdi limit. As such, the first peak controller 302 may have complete control over the loop in an embodiment and the medical practitioner may retain some control over the loop in another embodiment.

When the EAdi is within the range defined by the peak EAdi limit and the hysteresis value, the main controller 216 continuously monitors the peak EAdi of the patient. If the peak EAdi of the patient wanders beyond the range defined by the peak EAdi and the hysteresis value, for a time duration that exceeds the peak EAdi time out limit, the main controller 216 once again controls one or more of the sub-systems 110, 120 and 130 to return the peak EAdi of the patient to the peak EAdi limit.

An initial dosage of for the flow or respiratory gas may be determined from an expected ml/kg per body weight (PBW) tidal volume divided by a neural inspiratory time. The flow may then be adjusted via a closed loop until the target neural drive and tidal volume reduction is reached.

If an endotracheal tube is inserted deep into the airways of the patient, the flow tends to be stopped for an instant at the end of each neural inspiration. The pressure sensor 232 connected to the tip of the external flow delivery tube 238 where it reaches the endotracheal tube so that the pressure sensor 232 actually measures the pressure inside the patient's airways when the flow is interrupted. This pressure monitoring may be used to prevent that the flow generates excessive airway pressure at the end of the inspiratory phase.

Without limitation, the EAdi rise time may be determined as the period when EAdi increases, as shown on FIG. 3. The EAdi rise time may be presented as a mean, median or mode value for a given period and may be constantly updated. The EAdi rise time may be used for calculating the base flow for the delivery of respiratory gas to the patient. For example, using an expected tidal volume of 6 ml/kg PBW in a 3 kg baby and a 0.4-second EAdi rise time, the base flow for the respiratory gas may be set equal 18 ml for each 0.4-second period, which translates to 2.7 liters per minute.

The first peak controller 302 adjusts the flow or respiratory gas as follows. The respiratory flow is delivered toward the patient at the multiple of the base flow starting at the beginning of the inspiratory phase, the flow being reduced during the inspiratory phase so that it meets the base flow no later than the end of the inspiratory phase. The flow may be reduced gradually, exponentially, or in one or more steps, at various times during the inspiratory phase. The flow of respiratory gas continues being delivered toward the patient during the expiratory phase, for example at the base flow or at a somewhat lower flow. As mentioned hereinabove, the respiratory flow may be inhaled in part by the patient, but a significant portion of the respiratory flow may be leaked to the atmosphere.

As a non-limiting example, the adjustment would then be to increase the flow in the nasal flow catheter to this value or higher: where a flow factor 1 equals the base flow, a flow factor 2 equal 2 times the base flow (in this example 2 times 2.7 l/min i.e. 5.4 l/min, for the 3 KG baby). The adjustment of the assist may therefore be expressed in multiples of the base flow.

The flow of respiratory gas is thus highest at onset of the EAdi signal and is then reduced. For example, the flow may be adjusted such that the multiple is applied at onset of inspiration (e.g. 2 times the expected inspiratory flow), the flow then being until it is matching base normal inspiratory flow (i.e. 1 times the expected inspiratory flow). This allows a "high" flow delivery of near $CO_2$ free and $O_2$ enriched air from the nasal cannula 240 to the airways at the start of inspiration, facilitating washout of $CO_2$ from the airways and delivery of $O_2$ to airways when the lungs are deflated. At mid inspiration, the flow may approach the lower base flow and deliver near $CO_2$ free and $O_2$ enriched air until end of inspiration. The downregulation of the multiple applied to the base flow may take place either as a step or a linear or non-linear function. In its simplest version, the flow delivery may be set to a constant rate that remains throughout the entire EAdi rise time period. Maintained flow throughout the entire EAdi rise time may be used during positive pressure assist and airway $CO_2$ dilution.

The EAdi rise time is the period from onset the EAdi signal until it starts to decrease, as shown on FIG. 3. Due to the Hering Breuer inflation sensitive reflex, an inspiration with increased load is prolonged relative to a less loaded inspiration. Hence, application of an inspiratory pressure assist that increases transpulmonary (lung distending pressures) and volume would result in shorter neural inspiratory time to reach a volume than a breath without assist. The first peak controller 302 calculates the EAdi rise time on a neural breath by breath basis except during sighs (e.g. when the neural inspiration is greater than 1 second and the EAdi signal is greater than 10 µV), central apneas (e.g. when the neural expiration is greater than 5 seconds), and sub-ventilatory efforts (e.g. when EAdi efforts do not suffice to provide an inspiration), typically described by the cumulated EAdi over time. The first peak controller 302 causes the synchronized flow to be paused for a few breaths (or a time period) and compares the EAdi rise time between flow delivery and no flow delivery. In this example, the fraction of EAdi rise time during breaths with flow delivery is calculated as a percentage of those when flow delivery is paused. In the case where flow delivery does not generate airway pressure (i.e. does not expand lungs), the EAdi rise time is similar with or without flow delivery.

Figure 10:
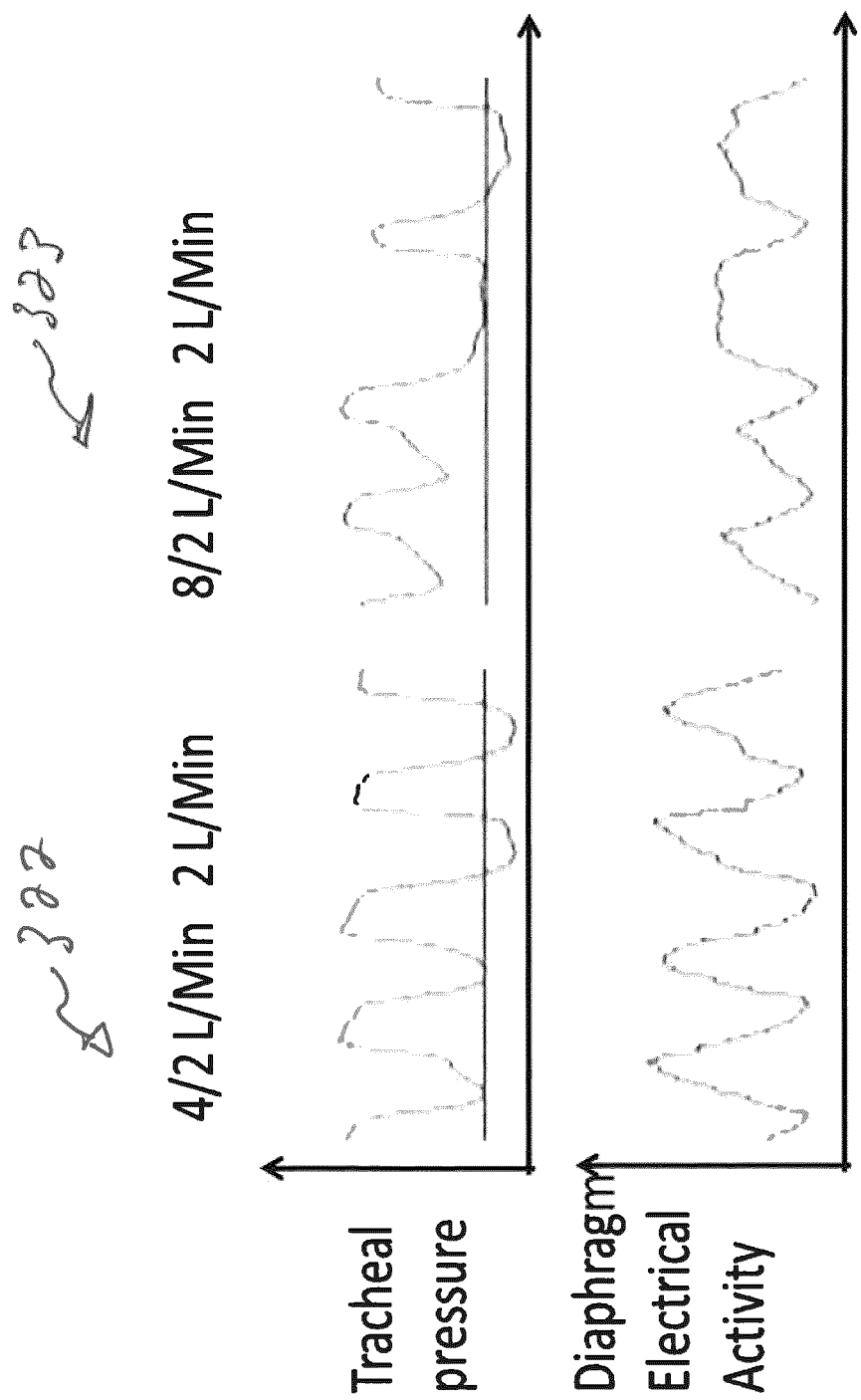
FIG. 10 is an example tracing of tracheal pressures and EAdi over time for a patient receiving synchronized airway $CO_2$ dilution.

FIG. 10 is an example tracing of tracheal pressures and EAdi over time for a patient receiving synchronized airway $CO_2$ dilution. In a first time period 322, for a patient whose base flow is 2 liters per minute, the respiratory gas is delivered at 4 liters per minute, i.e. with a multiple of two (2) for the entire duration of the inspiratory phase, returning to the base flow of 2 liters per minute in the expiratory phase. Then, in a second time period 323, the respiratory gas is delivered at 8 liters per minute, i.e. with a multiple of four (4) for the entire duration of the inspiratory phase, returning to the base flow of 2 liters per minute in the expiratory phase. Peaks of the EAdi are considerably reduced in the second time period 323. In the case that flow delivery increases airway pressure (i.e. inflates the lungs, the) EAdi rise time becomes shorter in comparison to breath when flow delivery is paused. Among the above mentioned parameter values inputted to the NRDV modulation system 100, one parameter is the limit for an increase of EAdi rise-time ($EAdi_{T-UP}$) that the first peak controller 302 uses to ensure that the EAdi rise-time does increase more than allowed by this parameter value. The first peak controller 302 maintains airway $CO_2$ dilution at a maximum effect at non-pressurising levels and prevents increasing lung-distending pressures and volumes.

Neural Control of Sub-Diaphragmatic Unloading

The negative pressure controller 258 synchronizes the operation of the proportional valve 260 with the patient's inspiration and delivers negative pressure having a magnitude that, for example, may be inversely proportional to the electrical activity of a patient's respiratory muscle, for example the patient's EAdi. Specifically, the magnitude of the negative pressure assist may be adjusted by a gain that converts the electrical activity of the patient's respiratory muscle, for example EAdi, into a negative pressure; this gain controlling the amount of pressure delivered for a given EAdi. The EAdi signal may be translated into pressure units by a gain controller in the negative pressure controller 258 and adjusted to generate negative pressure.

For example, for a gain of minus one (−1), an EAdi of 1 µV implies a pressure of −1 cm $H_2O$ and, for a gain of minus two (−2), the same EAdi of 1 µV implies a pressure of −2 cm $H_2O$.

The negative pressure may be applied in as a triangular waveform, a square waveform, or any other waveform that it is neurally triggered upon the start of the inspiratory phase and terminates at the end of the inspiratory phase.

Figure 11:
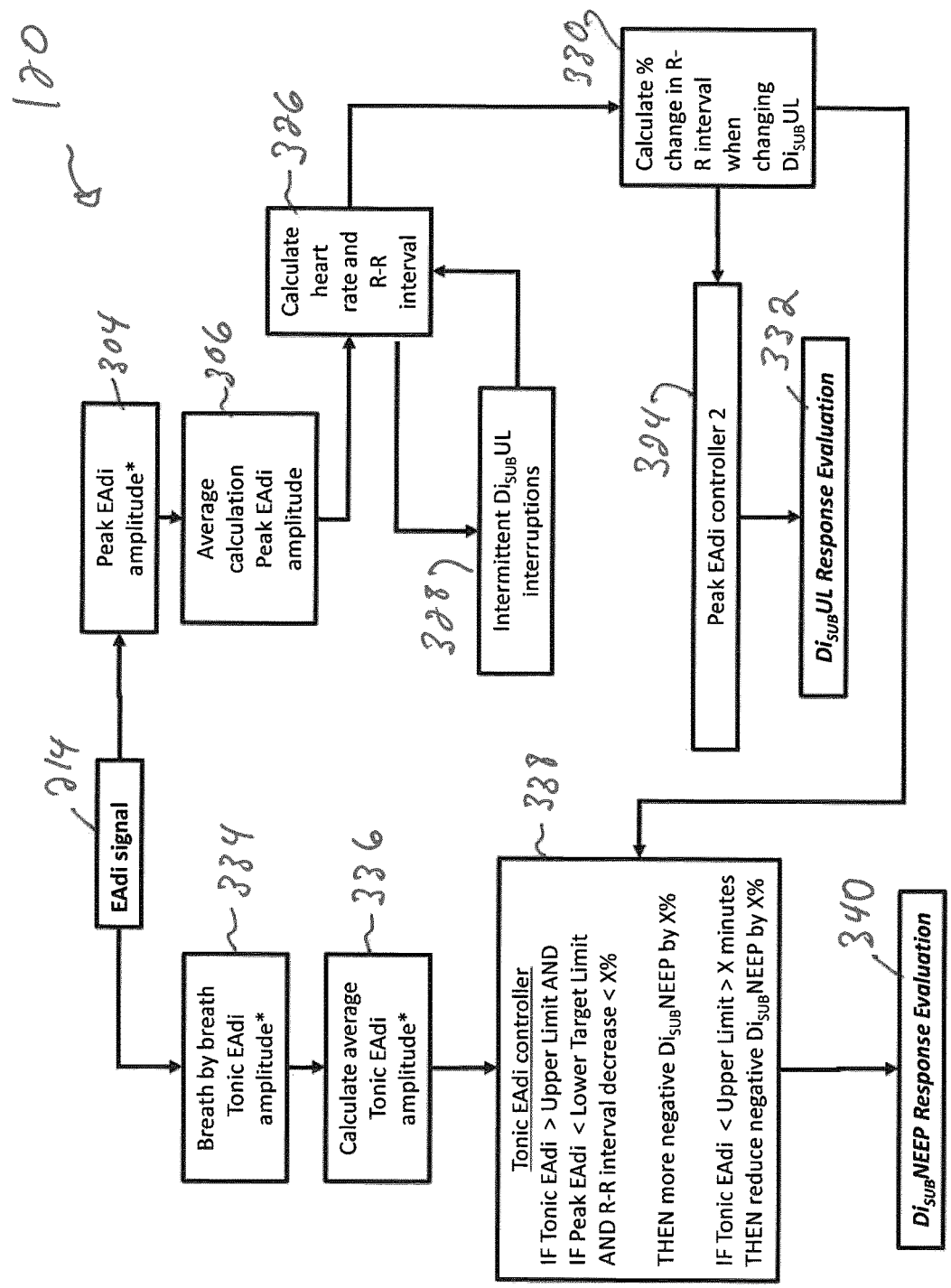
FIG. 11 is a block diagram of a synchronized sub-diaphragmatic unloading and sub-diaphragmatic negative end-expiratory pressure unloading sub-system according to an embodiment.

FIG. 11 is a block diagram of a synchronized sub-diaphragmatic unloading and sub-diaphragmatic negative end-expiratory pressure unloading sub-system according to an embodiment. FIG. 11 outlines closed loop neural feedback and reflex methods and systems used to control or guide adjustments for the sub-diaphragmatic unloading by the $Di_{SUB}UL$ and $Di_{SUB}NEEP$ sub-system 120. A second peak EAdi controller 324 is used to adjust a gain for multiplying the EAdi, if the assist is proportional, or a pressure waveform, if the assist is fixed during sub-diaphragmatic unloading. If the peak EAdi is greater than the peak EAdi limit, a negative gain or a negative pressure is increased (it is understood that the magnitude of the resulting negative pressure is to be increased). If the peak EAdi is less than peak EAdi limit, the negative gain or the negative pressure will be reduced (it is understood that the magnitude of the resulting negative pressure is to be decreased). The peak EAdi amplitude and the average thereof are calculated in the same manner as described in relation to FIG. 9. The heart rate and a corresponding R-R interval are calculated at 326. The second peak EAdi controller 324 causes the diaphragm unloading component 264 of the $Di_{SUB}UL$ and $Di_{SUB}NEEP$ sub-system 120 to apply the sub-diaphragmatic unloading.

The second peak EAdi controller 324 may also perform a test stage designed to evaluate a performance of the therapy. From time to time, the second peak EAdi controller 324 causes intermittent pauses 328 of the application of sub-diaphragmatic unloading, during which the heart rate and R-R interval are calculated again at 326. A change of the R-R interval during the pauses is calculated at 330, this change being for example expressed in terms of a percentage decrease of the R-R interval. This change is provided to the second peak EAdi controller 324 that produces an evaluation 332 of the sub-diaphragmatic unloading in view of adjusting the magnitude of the negative pressure, either directly or by adjusting the gain for multiplying the EAdi value.

Figure 12:
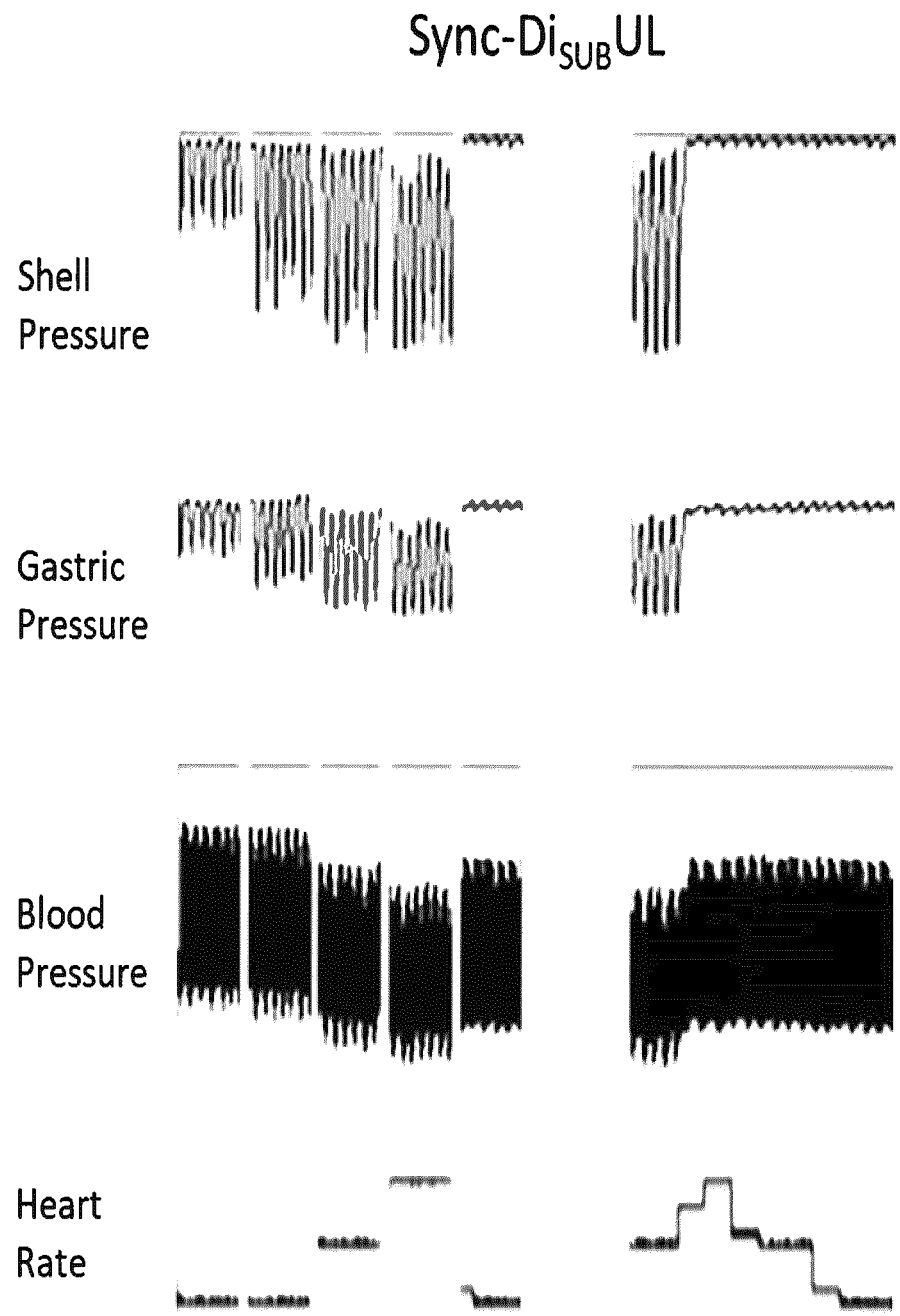
FIG. 12 shows physiological tracings of a patient receiving synchronized sub-diaphragmatic unloading.
Figure 13A:
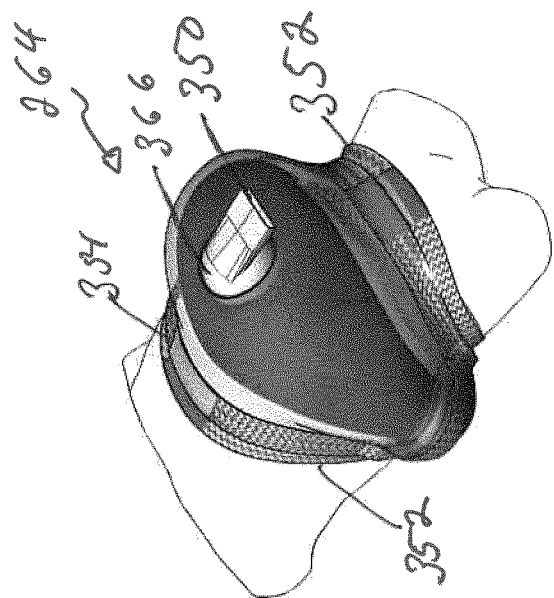
FIGS. 13a-d are illustrations of a device for abdominal unloading of a patient according to an embodiment.
Figure 13B:
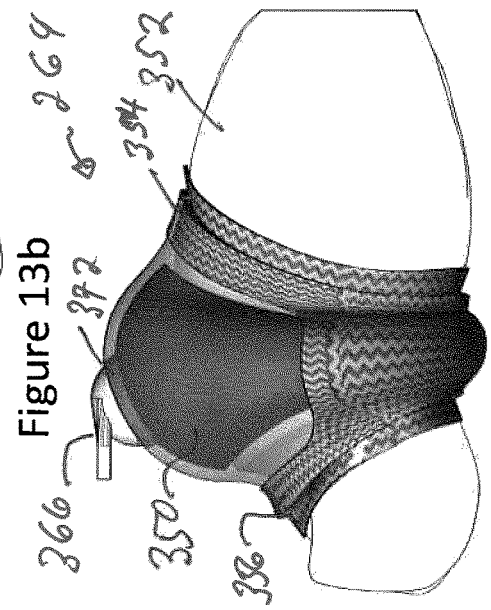
Figure 13C:
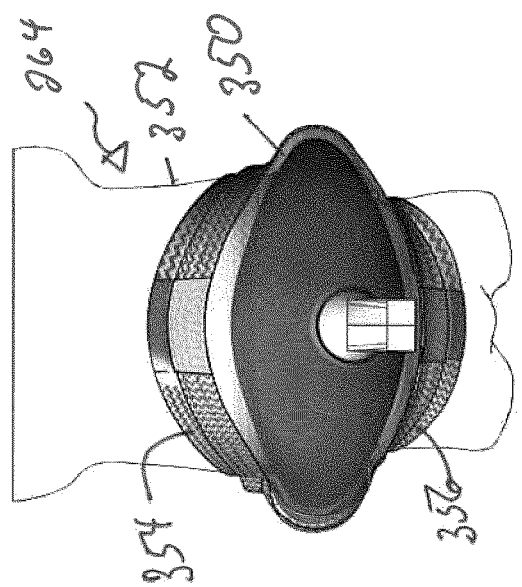
Figure 13D:
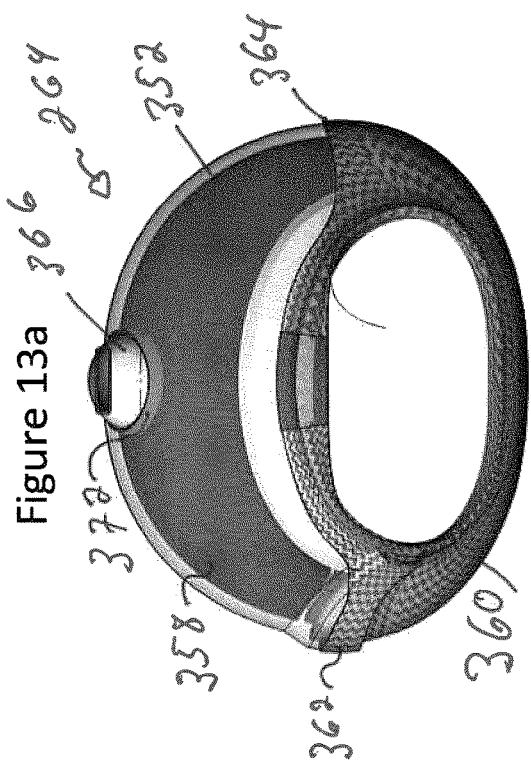

FIG. 12 shows physiological tracings of a patient receiving synchronized sub-diaphragmatic unloading. To control for hemodynamic adverse effects, the R-R interval is calculated from the tracings of electrical activity of the heart and of the diaphragm of the patient (FIG. 3). The R-R interval and the heart rate of patient are affected by changes in blood pressure (vagal reflex). An acute decrease of blood pressure decreases the R-R interval and increases the heart rate, and vice versa. Hence, the NRDV modulation system 100 uses the R-R interval to mitigate the effects of sub-diaphragmatic unloading on the hemodynamics of the patient.

In an embodiment, values of the R-R interval with and without sub-diaphragmatic unloading are compared. Following an acute removal of sub-diaphragmatic unloading, the NRDV modulation system 100 interprets a decrease of the R-R interval as a sign that sub-diaphragmatic unloading affects the hemodynamics of the patient. The second peak EAdi controller 324 instructs the $Di_{SUB}UL$ and $Di_{SUB}NEEP$ sub-system 120 to pause the application of sub-diaphragmatic unloading by the diaphragm unloading component 264 for a few breaths (or a for a predetermined time period) and compares the R-R interval with and without sub-diaphragmatic unloading. The limit for the increase of the R-R interval with and without sub-diaphragmatic unloading is used to determine at what gain level and/or negative end-expiratory pressure level the hemodynamics may be affected. The second peak EAdi controller 324 uses this limit in view of preventing hemodynamic adverse effects during negative end-expiratory pressure and sub-diaphragmatic unloading.

Generally speaking, the second peak EAdi controller 324 operates as follows. In a normal stage, it causes the application of a negative pressure on the abdomen of the patient during inspiratory phases of the patient. From time to time, it performs the above described test stage in which the application of the negative pressure on the abdomen of the patient is momentarily paused. The R-R interval is expected to decrease during this pause, when compared with the R-R interval when the negative pressure is normally applied. The second peak EAdi controller 324 therefore implements a loop that cycles between normal and test stages. The loop may be terminated or parameters of the normal stage may be modified as follows. The magnitude of the negative pressure is increased and the normal stage continues if the peak of the EAdi is greater than the peak EAdi limit and the decrease of the R-R interval is less than the R-R interval decrease limit. The magnitude of the negative pressure is decreased and the normal stage continues if the peak EAdi is less than the peak EAdi limit. The loop terminates if decrease of the R-R interval exceeds the R-R interval decrease limit or if the peak EAdi is in a range defined by the peak EAdi limit and the hysteresis value.

If an EAdi change contribution of less than 100% has been defined for the synchronized sub-diaphragmatic unloading, in which case either or both of the synchronized airway $CO_2$ dilution (AwCO$_2$Dil) sub-system 110 and the synchronized positive pressure assist and airway $CO_2$ dilution (AwPass&CO$_2$Dil) and airway positive end-expiratory pressure (AWPEEP) sub-system 130 also come into action, the second peak EAdi controller 324 determines an intermediate peak EAdi target for the synchronized sub-diaphragmatic unloading based on the EAdi change contribution and based on the EAdi change contributions assigned to the sub-systems 110 and 130. Also, in view of the EAdi change contribution being less than 100%, the above conditions are modified as follows. The magnitude of the negative pressure to be applied on the abdomen of the patient is increased if (i) the peak of the EAdi is greater than the peak EAdi limit, (ii) the peak EAdi is greater than the intermediate peak EAdi target, and (iii) the decrease of the R-R interval is less than the R-R interval decrease limit. The loop is terminated if the peak EAdi is less than the intermediate peak EAdi target. The magnitude of the negative pressure to be applied on the abdomen of the patient is decreased if (i) the peak EAdi is less than the peak EAdi limit and (ii) the peak EAdi is less than the intermediate peak EAdi target. The loop is terminated if (i) the peak EAdi is less than the peak EAdi limit and (ii) the peak EAdi is greater than the intermediate peak EAdi target. The loop is also terminated if the decrease of the R-R interval is greater than the R-R interval decrease limit. Finally, the loop is terminated if the peak EAdi is in a range defined by the peak EAdi limit and the hysteresis value. It is noted that, in an embodiment, the loop may be implemented on the basis of alarms and prompts provided on the operator interface 115 to assist a medical practitioner with suggestions to adjust a magnitude of the negative pressure to be applied on the abdomen of the patient when the peak EAdi is greater or smaller than the peak EAdi limit. As such, the second peak EAdi controller 324 may have complete control over the loop in an embodiment and the medical practitioner may retain some control over the loop in another embodiment.

When the EAdi has reached the range defined by the peak EAdi limit and the hysteresis value, the main controller 216 continuously monitors the peak EAdi of the patient. If the peak EAdi of the patient wanders beyond the range defined by the peak EAdi limit and the hysteresis value, for a time duration that exceeds the peak EAdi time out limit, the main controller 216 once again controls one or more of the sub-systems 110, 120 and 130 to return the peak EAdi of the patient to the peak EAdi limit.

The sub-diaphragmatic unloading is designed to accompany the airway $CO_2$ dilution because it unloads the diaphragm without increasing lung distending pressure. In fact it removes the work to displace abdominal contents during inspiration while providing support during expiration. In this way, lung volume and peak EAdi maybe reduced to a certain degree by airway $CO_2$ dilution and then further reduction in EAdi may be obtained with maintained sub-diaphragmatic unloading. Hence reductions in both neural respiratory drive and tidal volumes may be tailored individually for each patient.

Neural Control of Negative End-Expiratory Pressure (NEEP)

An increase of the EAdi activity during the neural expiratory period (when the EAdi is decreasing or at its lowest plateau) may be a sign that the lungs are collapsing during expiration and that the diaphragm should be kept active to prevent this; this effect is of particular interest in the case of newborn babies. By applying a negative pressure on the abdomen of the patient at the end of the expiratory phase, a reduction in tonic EAdi is expected if it satisfies the required lung recruitment. The above described technique for detecting the R-R decrease may be used to mitigate the potential side effects of the negative pressure on the hemodynamics of the patient.

In one embodiment, negative end-expiratory pressure may be applied at a fixed sub-diaphragmatic unloading negative pressure level.

In another embodiment, negative end-expiratory pressure (NEEP) may be controlled by the amplitude of the tonic EAdi 48 (shown on FIG. 3), which is the lowest EAdi value reached between breaths. Tonic EAdi 48 may be calculated as the lowest EAdi value on a neural breath by breath basis, except during central apneas (when the neural expiration exceeds five (5) seconds), and except during sub-ventilatory efforts. An average of the tonic EAdi may be calculated over a time period to guide an adjustment of negative end-expiratory pressure. The tonic EAdi upper limit is used to increase the magnitude of the negative end-expiratory pressure when the tonic EAdi upper limit is exceeded and to decrease the magnitude of the negative end-expiratory pressure when the tonic EAdi falls below the tonic EAdi upper limit for at least the tonic EAdi time out limit. This may help ensuring that lungs are appropriately recruited and to prevent VILI. The rate of decrease as well as ratio of time pre and post peak of the EAdi signal may also be used as indicators of lung de-recruitment.

The diaphragm unloading component 264 may be used to apply a negative end-expiratory pressure (NEEP). The EAdi signal 214 is also analysed to detect a breath by breath tonic EAdi amplitude 334. An average of the tonic EAdi amplitude is calculated at 336. A control function 338 of the tonic EAdi may increase a magnitude of the negative end-expiratory pressure to be applied on the abdomen of the patient if, concurrently, the tonic EAdi level is greater than a tonic EAdi limit, the peak of the EAdi is less than the peak EAdi limit, and the decrease of the R-R interval is less than the R-R interval decrease limit. The control function 338 may decrease the magnitude of the negative end-expiratory pressure to be applied on the abdomen of the patient if the tonic EAdi level is lower than the tonic EAdi limit for at least a predetermined duration. An evaluation of the response is made at 340 in view of adjusting the magnitude of the applied negative end-expiratory pressure.

Device for Abdominal Unloading of a Patient

FIGS. 13a-d are illustrations of a device for abdominal unloading of a patient according to an embodiment. The diaphragm unloading component 264 comprises a shell 350 that surrounds the entire abdomen 352 of the patient. The shell has flexible apical end 354 and caudal end 356 that respectively follow the anatomical structure of the lower ribcage and the upper pelvis. The function of the diaphragm unloading component 264 is to apply negative pressure encompassing the entire abdominal surface during inspiration. The diaphragm unloading component 264 allows depressurization of the abdomen during neural inspiration to remove some load to the diaphragm induced during its descent into the abdominal cavity.

The diaphragm unloading component 264 includes a central stabilizing exoskeletal structure covering the entire abdominal area of the lower torso that is not supported by the skeleton as outlined by the dark areas in FIGS. 13a-d. This exoskeleton section is not in contact with the skin of the patient. A decrease of the stiffness from the central area towards the lower ribcage and the upper pelvis provides a soft interface towards the body surfaces, at the apical and caudal ends 354 and 356. This interface to the body surface has a "collar design" that disperses pressure contact to the skin of the lower ribcage and the upper pelvis (lighter areas in FIGS. 13a-d). The most distal parts of the apical and caudal ends 354 and 356 are thin and soft such that both the apical and caudal ends 354 and 356 are sucked to the skin when negative pressure is applied.

Figure 15B:
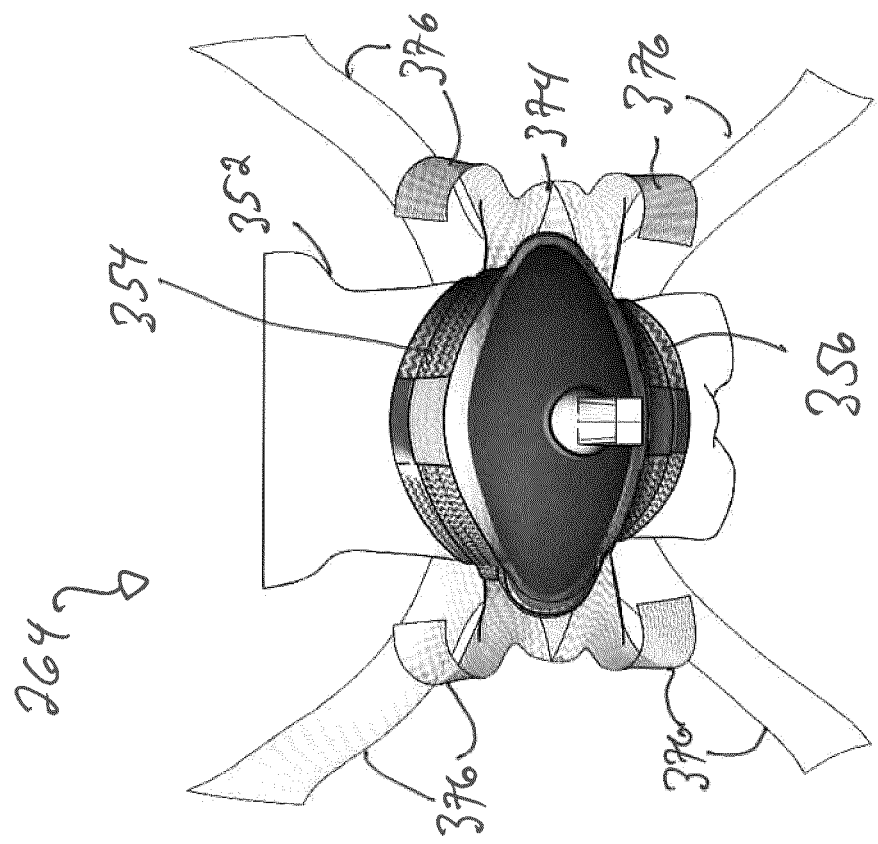
FIGS. 15*a-b* are illustrations of a sealing and protective film for use with the device of FIGS. 13*a-d;*
Figure 15A:
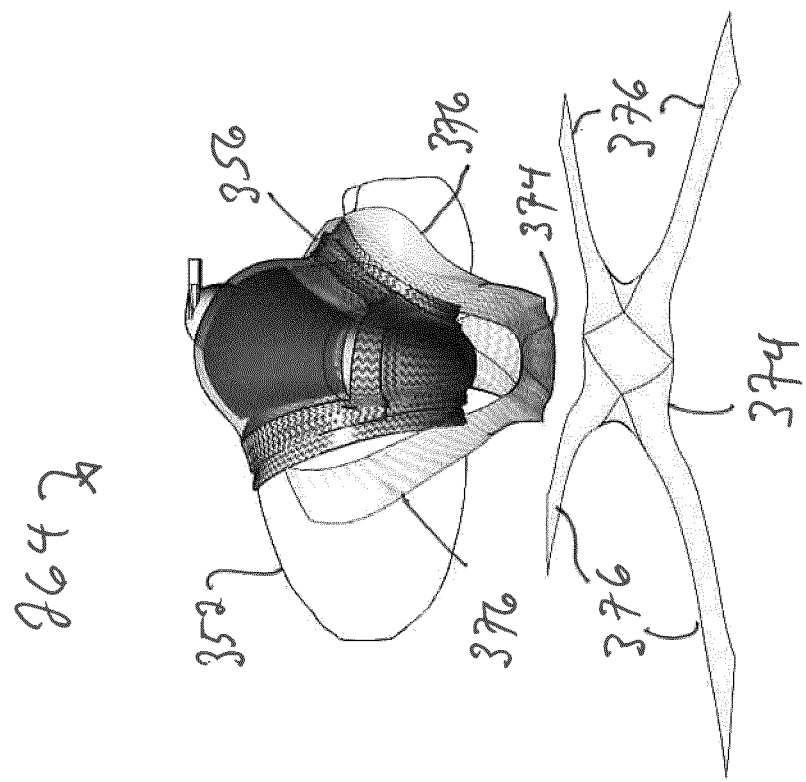

The apical and caudal ends 354 and 356 may be perforated to increase lateral compliance of the areas interfacing the skin. The leaks that this design might cause may be sealed by a protective film (FIGS. 15a-b).

The abdominal unloading shell is divided into a frontal section 358 and a dorsal section 360 to allow its placement around the abdomen 352 of the patient. On one side a flexible joint 362 is obtained by an interruption of the more rigid exoskeleton. A connection is maintained between the frontal and dorsal sections 358 and 360 via a continuation flexible material at the flexible joint 362. On a side 364 opposite from the flexible joint 362, the frontal and dorsal sections 358 and 360 are divided, such that the diaphragm unloading component 264 may be opened, the dorsal section 360 may be put under the patient, and then the frontal section 358 may be positioned over the abdomen 352 of the patient to close the diaphragm unloading component 264.

The diaphragm unloading component 264 provides a quite non-compliant chamber having very compliant interfaces that follow the upper and lower outlines of the abdomen 352 of the patient. Application of the protective film provides a self-sealing interface to the body that allows further reduction of tension and pressure on tissue and reduces risk of pressure sores. The division of frontal and dorsal sections 358 and 360 allowing opening and closing and easy mounting on the body of the patient.

Figure 14:
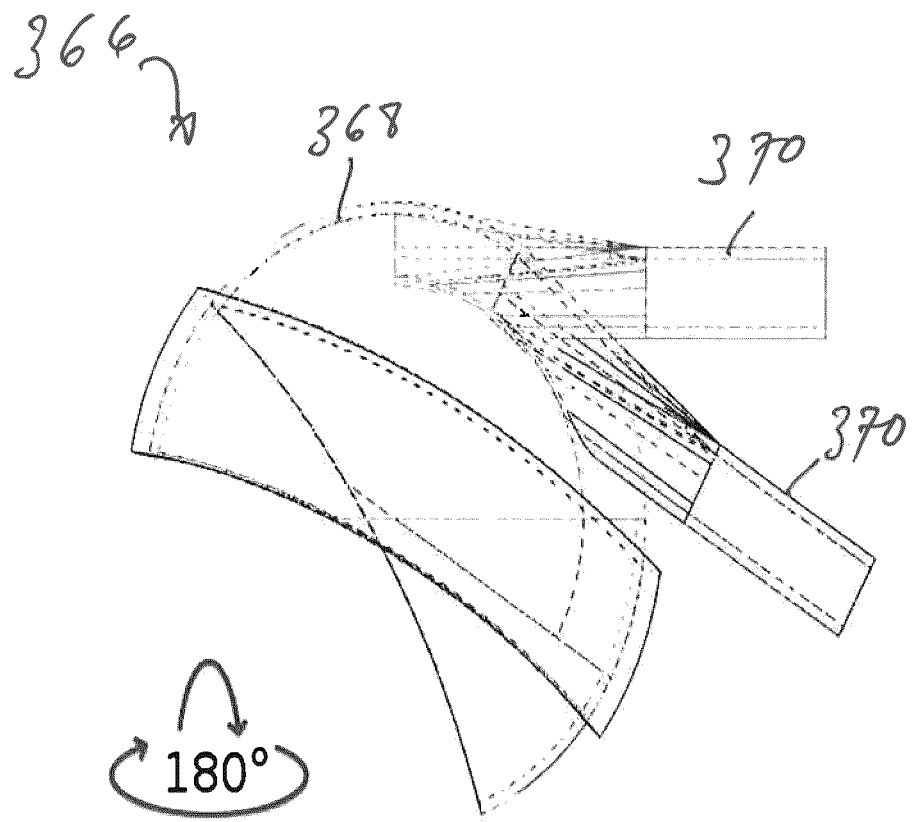
FIG. 14 is an illustration of an interface of the device of FIGS. 13*a-d* having an adjustable positioning.

FIG. 14 is an illustration of an interface of the device of FIGS. 13a-d having an adjustable positioning. A central area of the frontal section 358 of the shell comprises a hollow, ball-shaped interface 368. The interface 368 is open to the inside of the shell. The interface 368 comprises, on the outside of the shell, a flat hollow connector part 370. This connector part 370 is adapted to mate with the negative pressure tube 262 (FIG. 7) that delivers the negative pressure. The connector part 360 allows adjustable positioning. Otherwise stated, the connector part 370 may be rotated and its angle may be changed in at least two (2) dimensions, as shown on FIG. 14. The connector part 370 is placed in a fitting round groove 372 of the diaphragm unloading component 264 and is adapted to seal when negative pressure is applied on the diaphragm unloading component 264 via the negative pressure tube. A second thin tube (not shown) used as a pressure sensing tube is attached to or imbedded in the negative pressure tube 262. One end of the pressure sensing tube enters inside the shell. An opposite end of the pressure sensing tube is connected to a pressure sensor that provides a measurement of the actual pressure inside the diaphragm unloading component 264.

When the diaphragm unloading component 264 is connected to the negative pressure source, the adjustable connector part 270 allows suitable positioning of negative pressure tube 262 in view of the position of the patient. In addition to the pressure sensor, other sensors may be integrated in or connected to the diaphragm unloading component 264. It is contemplated that sensors used for measurement of abdominal distension and electro-cardiogram (ECG) could be incorporated in the shell. In a variant, an ultraviolet light used for treating newborn jaundice may be incorporated within the shell. Photo technology for measurement of abdominal respiratory movement may also be integrated to measure tidal volume displacement.

FIGS. 15a-b are illustrations of a sealing and protective film for use with the device of FIGS. 13a-d. When closing the abdominal shell, proper sealing may be maintained by affixing a protective film 374 having sleeves 376 that are wrappable on the apical end 354 and caudal end 356 of on the diaphragm unloading component 264. When installed, the protective film 374 forms an overlapping structure on the frontal and dorsal sections 358 and 360 that self-seals when negative pressure is applied on the diaphragm unloading component 264.

Once the frontal and dorsal sections 358 and 360 of the shell are mounted on the abdomen 352 of the patient, the protective film 374 may be applied. This protective film 374 substantially covers the entire dorsal section 360 of the shell, reaching below and above the shell. The sleeves 376 of the protective film 374 may be placed over the rib cage and pelvic parts of the frontal section 358 of the shell. The protective film 374 prevents leaks between skin and shell, and seals perforations used to increase compliance and fitting of the apical and caudal ends 354 and 356 with minimally applied tension around the pelvis or ribcage. The protective film 374 also protects the shell from urine and faeces.

Positive Pressure Assist and Airway $CO_2$ Dilution for Neural Drive and Tidal Volume Reduction Positive pressure assist and airway $CO_2$ dilution may be used to provide positive pressure ventilation jointly with synchronized airway $CO_2$ dilution. The positive pressure may be generated by adding a facial interface, such as a face mask, to the nasal cannula 240. A pressure controller and a valve may be used to control a level of the positive pressure ventilation.

Figure 16:
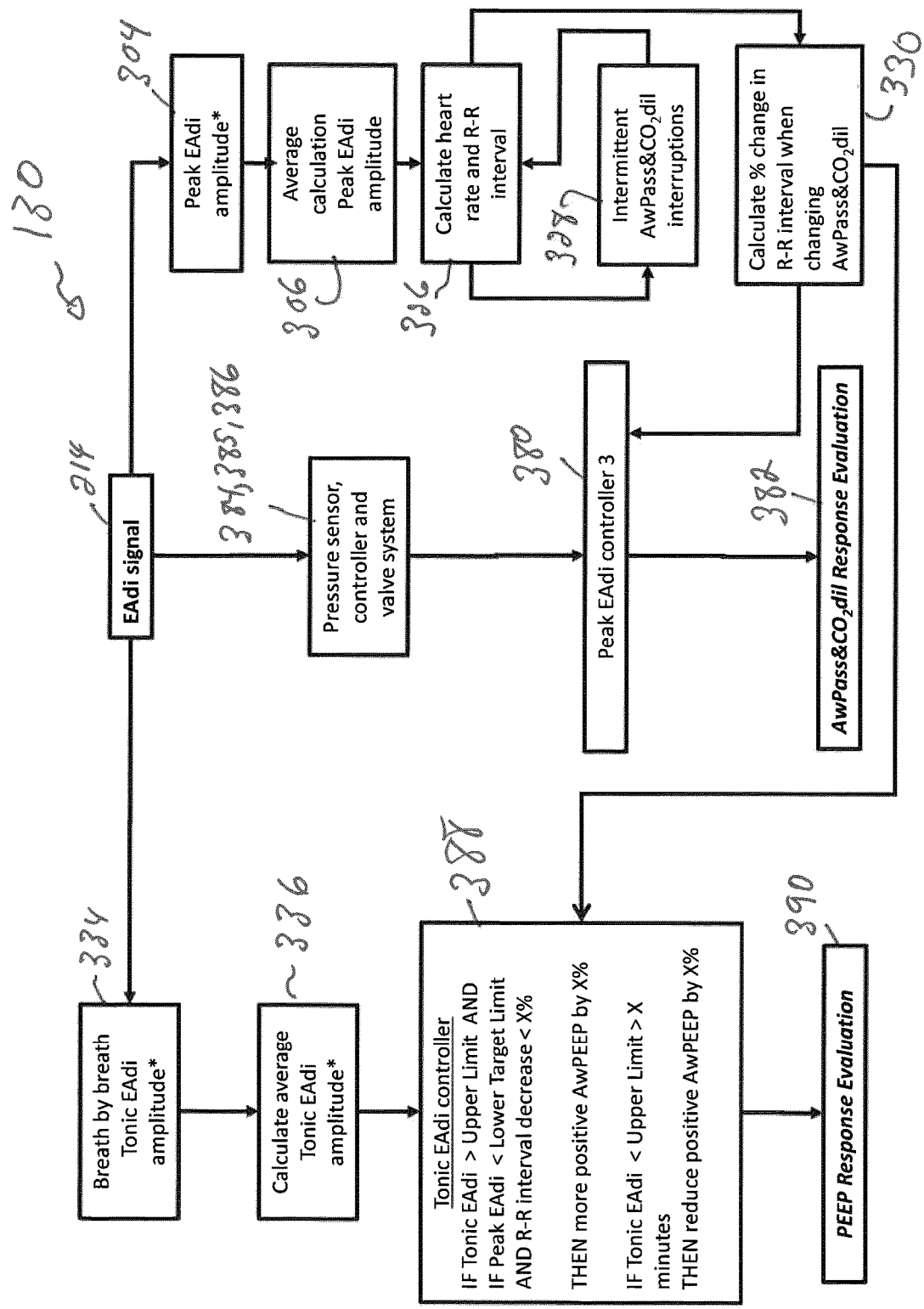
FIG. 16 is a block diagram of a synchronized positive pressure assist and airway $CO_2$ dilution and airway positive end-expiratory pressure sub-system according to an embodiment.

FIG. 16 is a block diagram of a synchronized positive pressure assist and airway $CO_2$ dilution and airway positive end-expiratory pressure sub-system 130 according to an embodiment. FIG. 16 outlines closed loop neural feedback and reflex methods and systems used to control or guide adjustments for the positive pressure assist and airway $CO_2$ dilution. A third peak EAdi controller 380, which is a local controller for the sub-system 130, is used to adjust a gain if the assist is proportional, or to control a pressure waveform if the assist is fixed during positive pressure assist and airway $CO_2$ dilution. If the peak EAdi is greater than the peak EAdi limit, a positive gain or a positive pressure is increased. If the peak EAdi is less than peak EAdi limit, the gain or the pressure is reduced. The peak EAdi amplitude and the average thereof are calculated in the same manner as described in relation to FIGS. 9 and 11. The heart rate, the R-R interval and the change of the R-R interval are obtained as described in relation to FIG. 11. The change of the R-R interval is provided to the third peak EAdi controller 380 that produces an evaluation 382 of the positive pressure assist and airway $CO_2$ dilution in view of adjusting the positive pressure, either directly or by adjusting the gain for multiplying the EAdi value. The third peak EAdi controller 380 controls the positive pressure using a pressure sensor 384, a controller 385 of the pressure in the airways of the patient, and a proportional valve 386 that causes a partial restriction of an expiratory flow from the patient.

The positive pressure may be applied as a triangular waveform, a square waveform, or in any other waveform that is neurally triggered and cycled-off.

Generally speaking, the third peak EAdi controller 380 operates as follows. In a normal stage, it causes the application of a positive pressure on the airways of the patient. From time to time, it may perform a test stage designed to evaluate a performance of the therapy. In the test stage, the application of the positive pressure on the airways of the patient is momentarily paused. The R-R interval is expected to decrease during this pause, when compared with the R-R interval when the positive pressure is normally applied. The third peak EAdi controller 380 therefore implements a loop that cycles between normal and test stages. The loop may be terminated or parameters of the normal stage may be modified as follows.

Initially, an EAdi change contribution of less than 100% has been defined for the synchronized sub-diaphragmatic unloading sub-system 120 and either or both of the synchronized airway $CO_2$ dilution (AwCO$_2$Dil) sub-system 110 and the synchronized positive pressure assist and airway $CO_2$ dilution (AwPass&CO$_2$Dil) and airway positive end-expiratory pressure (AWPEEP) sub-system 130 also come into action. The third peak EAdi controller 380 determines an intermediate peak EAdi target for the synchronized sub-diaphragmatic unloading based on the EAdi change contribution and based on the EAdi change contributions assigned to the sub-systems 110 and 130. The positive pressure to be applied on the airways of the patient is increased if (i) the peak of the EAdi is greater than the peak EAdi limit, (ii) the peak EAdi is greater than the intermediate peak EAdi target, and (iii) the decrease of the R-R interval is less than the R-R interval decrease limit. The loop is terminated if the peak EAdi is less than the intermediate peak EAdi target. The positive pressure to be applied on the airways of the patient is decreased if (i) the peak EAdi is less than the peak EAdi limit and (ii) the peak EAdi is less than the intermediate peak EAdi target. The loop is terminated if (i) the peak EAdi is less than the peak EAdi limit and (ii) the peak EAdi is greater than the intermediate peak EAdi target. The loop is also terminated if the decrease of the R-R interval is greater than the R-R interval decrease limit. Finally, the loop is terminated if the peak EAdi is in a range defined by the peak EAdi limit and the hysteresis value.

When the EAdi has reached the range defined by the peak EAdi limit and the hysteresis value, the main controller 216 continuously monitors the peak EAdi of the patient. If the peak EAdi of the patient wanders beyond the range defined by the peak EAdi limit and the hysteresis value, for a time duration that exceeds the peak EAdi time out limit, the main controller 216 once again controls one or more of the sub-systems 110, 120 and 130 to return the peak EAdi of the patient to the peak EAdi limit.

Neural Control of Airway Positive End-Expiratory Pressure (PEEP)

An increase of the EAdi activity during the neural expiratory period (when the EAdi is decreasing or at its lowest plateau) may be a sign that the lungs are collapsing during expiration and that the diaphragm should be kept active to prevent this; this effect is of particular interest in the case of newborn babies. By applying a positive pressure on the airways of the patient at the end of the expiratory phase, a reduction in tonic EAdi is expected if it satisfies the required lung recruitment. The above described technique for detecting the R-R decrease may be used to mitigate the potential side effects of the positive pressure on the hemodynamics of the patient.

In one embodiment, positive end-expiratory pressure may be applied at a fixed positive pressure level.

In another embodiment, positive end-expiratory pressure (PEEP) may be controlled by the amplitude of the tonic EAdi 48. The EAdi signal 214 is analysed to obtain the EAdi amplitude in the same manner as described in relation to FIG. 11. A control function 388 of the tonic EAdi may increase the positive end-expiratory pressure to be applied on the airways of the patient if, concurrently, the tonic EAdi level is greater than a tonic EAdi limit, the peak of the EAdi is less than the peak EAdi limit, and the decrease of the R-R interval is less than the R-R interval decrease limit. The control function 388 may decrease the positive end-expiratory pressure to be applied on the airways of the patient if the tonic EAdi level is lower than the tonic EAdi limit for at least a predetermined duration. An evaluation is made of the response is made at 390 in view of adjusting the positive end-expiratory pressure.

As in the case of the application of negative end-expiratory pressure on the abdomen of the patient, the application of positive end-expiratory pressure on the airways of the patient may help ensuring that lungs are appropriately recruited and to prevent VILI.

Facial Interface

Figure 17:
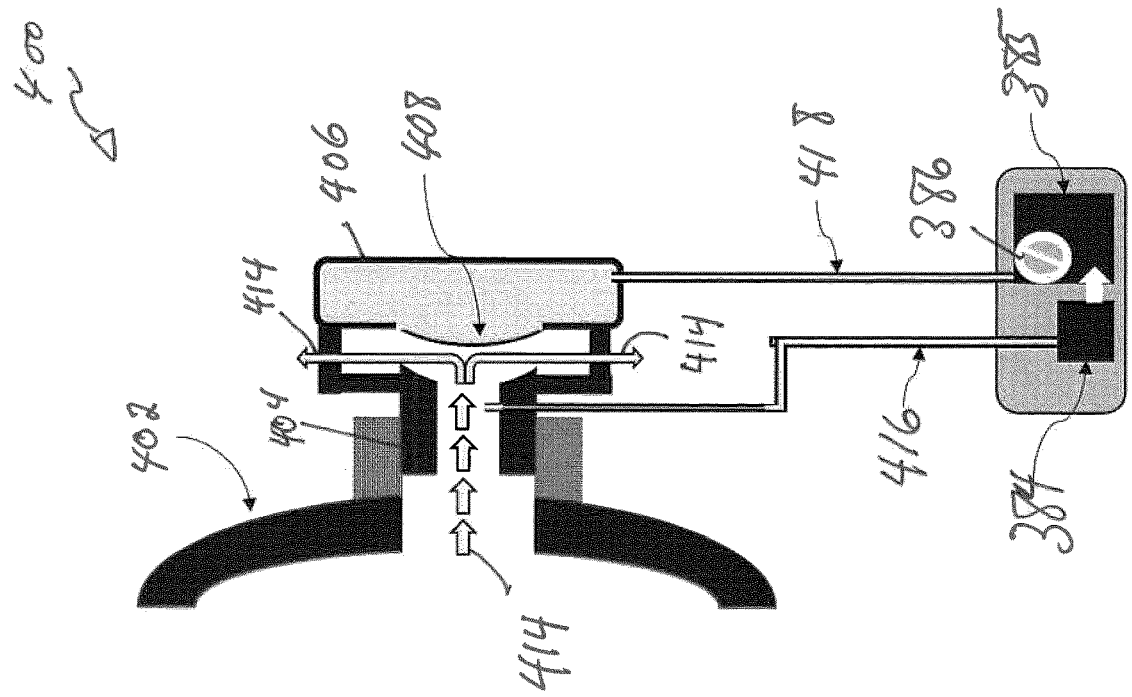
FIG. 17 is a block diagram of a facial interface according to an embodiment.
Figure 17:
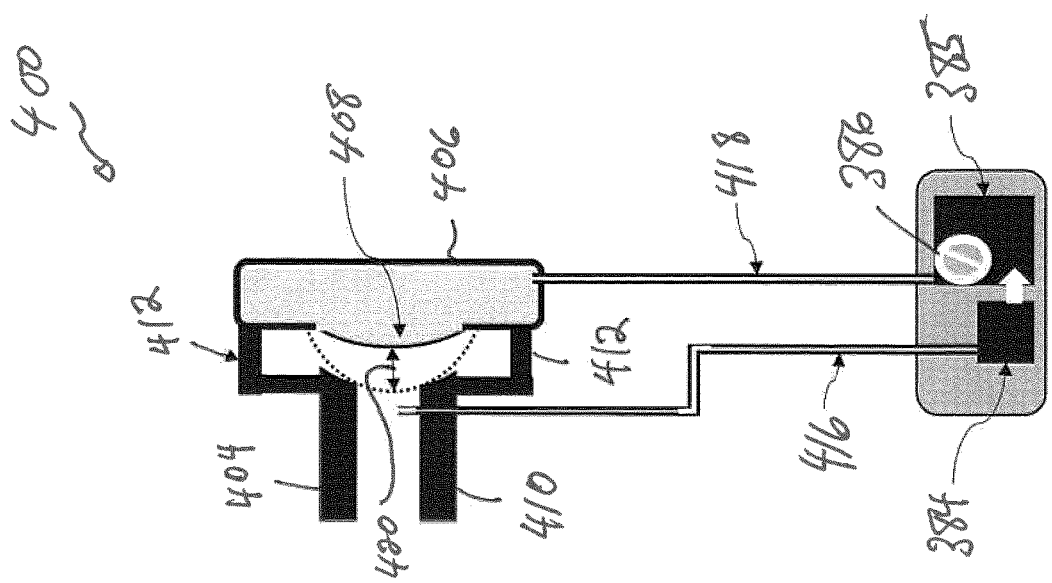

FIG. 17 is a block diagram of a facial interface according to an embodiment. A facial interface 400 uses the pressure sensor 384, the pressure controller 385, and the proportional valve 386 introduced in the discussion of FIG. 16. The facial interface 400 includes a face mask 402 adapted for placement on the face of the patient, and a connecting interface 404 linking the face mask 402 to a box 406 having a pressure controlled diaphragm 408. The connecting interface 404 has a first section 410 and a second section 412. The first section 410 may be selectively blocked at least in part by the diaphragm 408. The second section 410 includes apertures allowing an expiratory flow 414 of the patient to be expelled when the diaphragm 408 is not under pressure.

A sensing tube 416 connects the pressure sensor 384 to the first section 410 of the connecting interface 404 so that the pressure sensor 384 can detect the pressure in the airways of the patient. A pressurizing tube 418 connects the proportional valve 386 to the box 406 so that the pressure controller 385 may selectively cause the proportional valve 386 to apply a pressure inside the box 406, causing a movement 420 of the diaphragm 408 in view of selectively restricting the expiratory flow 414 of the patient.

As expressed hereinabove, when using the synchronized airway $CO_2$ dilution (AwCO$_2$Dil) sub-system 110 alone of with the synchronized positive pressure assist and airway $CO_2$ dilution (AwPass&CO$_2$Dil) and airway positive end-expiratory pressure (AWPEEP) sub-system 130, the NRDV modulation system 100 delivers a flow of respiratory gas to the patient, for example via the nostrils of the patient, the flow being set at the start of each inspiratory phase to multiple of the base flow that the patient is expected to need. The flow of respiratory gas continues being delivered to the patient at the base flow or a lower flow during the expiratory phase. Hence, the expiratory flow 414 is continuously present, combining the excess of the flow delivered to the patient at the start of the inspiratory phase, the flow that continues being delivered to the patient during the expiratory phase and, of course, the gases that are actually exhaled by the lungs of the patient. An example of a suitable nasal patient interface is found in International Patent Application Publication no WO 2018/0231128 published on Dec. 20, 2018 to Ahlmén, the disclosure of which being incorporated by reference herein.

The third peak EAdi controller 380 may cause the pressure controller 385 to apply a controlled pressure on the diaphragm 408. The diaphragm 408 moves to restrict at least in part the expiratory flow 414 from the patient. In this manner, an amount of flow resistance controlled by the third peak EAdi controller 380 and by the pressure controller 385 is applied on the facial interface 400, resulting in the positive pressure applied to the airways of the patient. This action on the facial interface 400 does not impede the delivery of the flow of respiratory gas to the patient controlled by the first peak EAdi controller 302.

The third peak EAdi controller 380 causes the facial interface 400 to induce a positive pressure that, for example, may be proportional to the electrical activity of a patient's respiratory muscle, the EAdi signal being multiplied by a gain. For example, for a gain of one (1), an EAdi of 1 µV implies a pressure of −1 cm $H_2O$ and, for a gain of two (2), the same EAdi of 1 µV implies a pressure of −2 cm $H_2O$.

Monitoring

Figure 18:
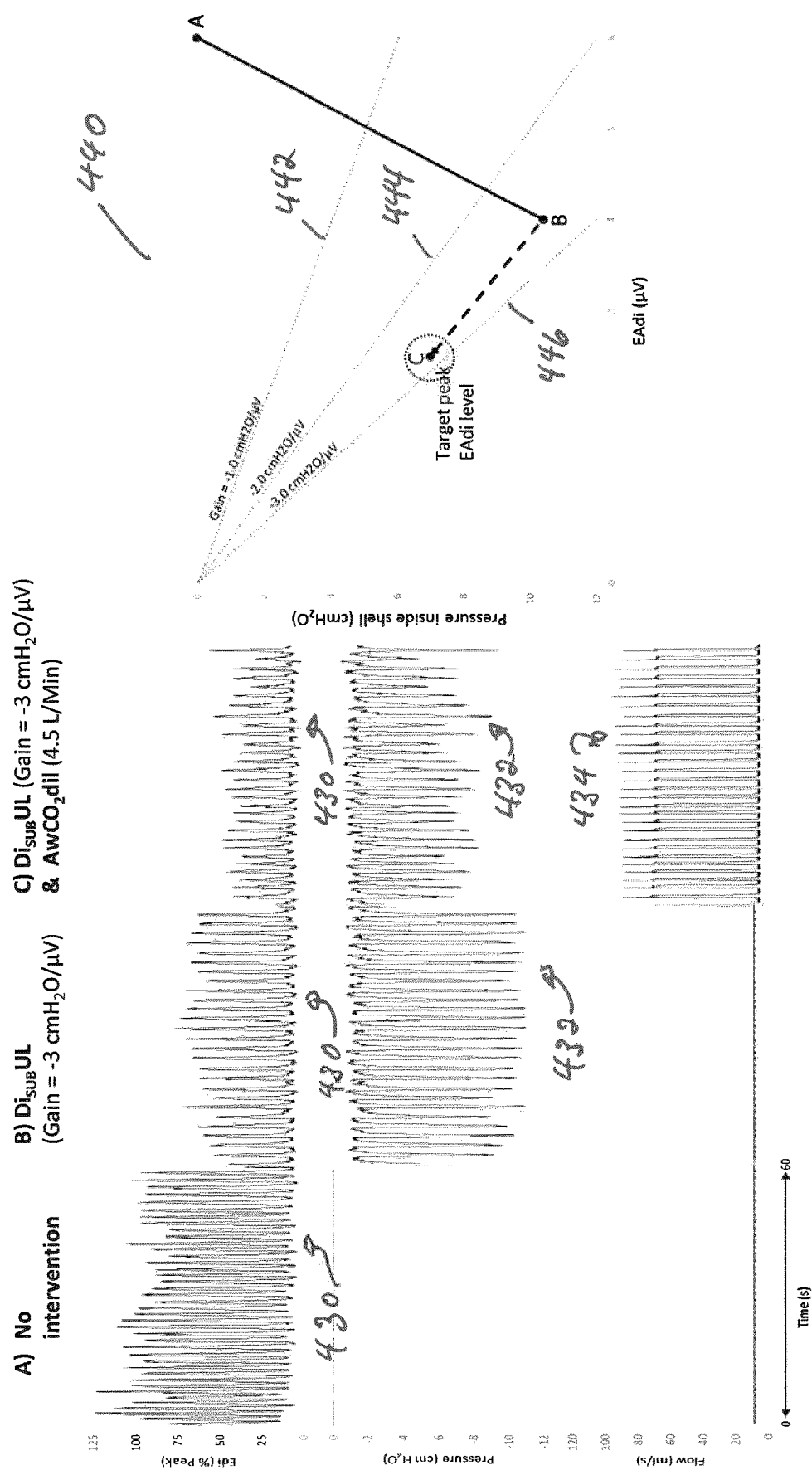
FIG. 18 is a group of graphs obtained using the NRDV modulation system to provide respiratory assist to a patient.

FIG. 18 is a group of graphs obtained using the NRDV modulation system to provide respiratory assist to a patient. The monitor 218 (FIG. 7) may for example display tracings 430 of the EAdi expressed in percentages of an initial average peak EAdi value, tracings 432 of the negative pressure applied on the abdomen of the patient, expressed in cm $H_2O$ (negative values), and tracings 434 of the of the flow of inspiratory gas delivered toward the airways of the patient, expressed in ml per second.

On FIG. 18, a first 60-second section (A) shows variations of the EAdi signal at a time when the NRDV modulation system 100 does not intervene. The peak EAdi is very high in the first section (A). In a second 60-second section (B), the NRDV modulation system 100 only applies the negative pressure on the abdomen of the patient, the magnitude of the pressure varying in synchrony with the EAdi signal. At that time, a gain of −3 cm $H_2O$ per µV is used to control the magnitude of the negative pressure. The peak EAdi is somewhat reduced in the section (B). In a third 60-second section (C), while the application of the negative pressure on the abdomen of the patient continues with the same gain, the NRDV modulation system 100 also applies the delivery of the inspiratory flow toward the airways of the patient, this delivery also varying in synchrony with the EAdi signal. It may be observed on the tracing 434 that the inspiratory flow as high as about 90 ml per second at the beginning of each inspiratory phase, then reducing to a base flow of about 75 ml per second, or equivalently 4.5 liters per minute. The peak EAdi is significantly reduced in this third section (C).

On a right-hand part of FIG. 18, a graph 440 shows that an initial peak EAdi value of 6 µV is present in the first section (A), when no negative pressure is applied on the abdomen of the patient. Curves 442, 444 and 446 shows predicted changes of the peak EAdi for various gains used to calculate the negative pressure. In the second section (B), the EAdi has reduced to about 4 µV, which is still above the peak EAdi limit in this example. In the third section (C), the peak EAdi has reached the peak EAdi limit that, in this example, is set to about 2.4 µV. The negative pressure is about −7.2 cm $H_2O$, this value being consistent with the peak EAdi value and the gain of −3 cm $H_2O$ per µV.

Monitoring of the NRDV modulation system's effect on the patient is demonstrated in FIG. 18. Left side, shows breath-by-breath EAdi (upper panel), breath-by-breath negative pressure applied around the abdomen inside the shell, and breath-by-breath flow applied at the nostril. Three conditions of 60 seconds each are presented: A) No assist, B) sub-diaphragmatic unloading, and C) airway $CO_2$ dilution in tandem with sub-diaphragmatic unloading. It may be observed that the highest EAdi (neural respiratory drive) occurs at A) when there is no mechanical or chemical unloading. Then at B) sub-diaphragmatic unloading reduces the EAdi. Finally, at C) airway $CO_2$ dilution addition to sub-diaphragmatic unloading not only further reduces the EAdi but also the negative pressure inside the shell.

The Integrated NRDV Modulation System

Without limiting the generality of the above disclosure, an embodiment of the NRDV modulation system 100 may use information from the EAdi signal exclusively as a closed loop controller for:

I) Airway $CO_2$ dilution to obtain airway $CO_2$ dilution for chemical unloading and reduction of respiratory drive, lung distending pressures and volumes. Insufficient $CO_2$ elimination may force end-inspiratory lung distending pressures and volumes to increase above acceptable limits. Airway $CO_2$ dilution acts to supply fresh gas into airways and dilute airway $CO_2$ concentration due to large leaks rendering pressures in the trachea insignificant. This chemical unloading reduces respiratory drive, end-inspiratory lung-distending pressures and volumes.

II) Sub-diaphragmatic unloading to unload the inspiratory muscles by overcoming mechanical loads using synchronized sub-diaphragmatic negative pressure assist specifically directed towards the abdomen preventing increase of lung distending pressure and volumes.

III) Negative end-expiratory pressure to interact with sub-diaphragmatic unloading and apply lung recruitment during neural expiration and preventing lungs from collapsing.

IV) Positive pressure assist and airway $CO_2$ dilution to generate positive airway pressure to unload respiratory muscles and reduce respiratory drive by taking advantage of excess flow administered by airway $CO_2$ dilution. If $CO_2$ induced respiratory drive is reduced, the Positive pressure assist and airway $CO_2$ dilution would utilize a facial interface and expiratory flow controller to control airway pressure without much increase of lung distending pressure but rather with unloading of the respiratory muscles and reduction of the respiratory drive.

V) Airway PEEP interaction with Positive pressure assist and airway $CO_2$ dilution and to apply lung recruitment during neural expiration and preventing lungs from collapsing.

The NRDV modulation system 100 does not require tracheal intubation and is entirely controlled by the EAdi signal. In fact, the combined unloading efficiency of sub-diaphragmatic unloading and airway $CO_2$ dilution and/or positive pressure assist and airway $CO_2$ dilution is comparable to that of conventional positive pressure systems using endotracheal tube inserted into the trachea. NRDV modulation provides a non-invasive control over both mechanical and chemical unloading providing means to unload inspiratory muscles as well as control end-inspiratory lung-distending pressures and volumes at the same time. Moreover, the system provides monitoring of the systems respective unloading functions.

The NRDV modulation system 100 may calculate:

1. The EAdi rise time on a neural breath by breath basis except during sighs (neural inspiration>1 s and >10 µV), central apneas (neural expiration>5 s), and sub-ventilatory efforts (i.e. EAdi efforts that do not suffice to provide an inspiration, typically described by the cumulated EAdi over time. The NRDV modulation system 100 instructs the synchronized flow (airway $CO_2$ dilution) to be paused for a few breaths (or a time period basis) and compares the EAdi rise time between flow delivery and no flow delivery. In this example the fraction of EAdi rise time is calculated during breaths with flow delivery as percentage of those when flow delivery is paused. In the case that flow delivery does not generate airway pressure (i.e. does not expand lungs), the EAdi rise time is similar with or without flow delivery. In the case that flow delivery increases airway pressure (i.e. inflates the lungs), the EAdi rise time will be prolonged when flow delivery is paused. The input variable for this calculation is a percent limit describing how much acute removal of flow delivery is allowed to increase the EAdi rise time. In other words, a flow delivery that increases pressurisation of the lungs is detected. Hence, it is possible to maintain airway $CO_2$ dilution at maximum effect at non-pressurising levels and prevent increasing lung distending pressures and volumes.

2. Peak EAdi amplitude, defined as the highest EAdi of a breath, is obtained on a neural breath by breath basis (breath by breath neural inspiration, expiration and duration is registered for every breath), except during sighs (neural inspiration>1 s and >10 µV), central apneas (neural expiration>5 s), and sub-ventilatory efforts and is used to calculate an average over time representing the neural respiratory drive. A target input value with upper and lower limits (in this case expressed as percentages) is used to adjust both flow delivery and sub-diaphragmatic unloading. The EAdi amplitude within its limits ensures adequate conditioning of the diaphragm to maintain muscle function, thereby preventing VIDD.

3. Tonic EAdi amplitude, the lowest EAdi between breaths, is calculated on a neural breath by breath basis (lowest EAdi is logged for every breath), except during central apneas (neural expiration>5 s), and sub-ventilatory efforts. The mean value for a time period is used to calculate an average tonic EAdi and guide adjustment of negative end-expiratory pressure. This aids in ensuring that lungs are appropriately recruited, thereby preventing VILI 4. The R-R interval and instantaneous heart rate is calculated from the ECG waveform from the unprocessed myoelectrical signals obtained in the esophagus. For example, summing all electrode channels cancels out the EAdi and amplifies the ECG obtained from the electrode pairs. An ECG waveform counter logs every ECG to ECG waveform duration). The R-R wave interval of the electrocardiogram is affected by changes in blood pressure (vagal reflex). For example, an acute decrease of blood pressure decreases the R-R interval i.e. increased heart rate, and vice versa. Hence, the R-R interval is used to prevent sub-diaphragmatic unloading from affecting the hemodynamics. In this example the R-R interval with and without sub-diaphragmatic unloading is compared. If acute removal of sub-diaphragmatic unloading decreases R-R interval, it is interpreted as sub-diaphragmatic unloading affects hemodynamics. The NRDV modulation system 100 instructs the sub-diaphragmatic unloading to be paused for a few breaths (or a time period) and compares the R-R interval with and without sub-diaphragmatic unloading. A limit for the percent increase of R-R interval with and without sub-diaphragmatic unloading is used to determine at what gain level and/or negative end-expiratory pressure level the hemodynamics are affected. This technique helps preventing hemodynamic adverse effects during negative end-expiratory pressure and sub-diaphragmatic unloading.

Example of the Closed Loop Control by NRDV Modulation System

In a non-limiting embodiment, to control the neural inspiration the NRDV modulation system 100 may either use airway $CO_2$ dilution to primarily reduce neural respiratory drive "chemically", reducing lung distending pressure and tidal volume. In such case, there is no "mechanical" unloading involved. Then NRDV modulation may use sub-diaphragmatic unloading and/or positive pressure assist and airway $CO_2$ dilution to primarily reduce the "mechanical" work. The below description exemplifies options to accomplish a target reduction in respiratory drive with a target reduction in volume but with relatively maintained lung distending pressure and tidal volume.

In this example, the control is aimed to initially "chemically" modulate neural respiratory drive, lung distending pressures and tidal volume and to then "mechanically" unload neural respiratory drive and work.

In this example, the intent is to reduce neural drive by about 50% and tidal volume by about 25%, starting at a peak EAdi of about 40 µV:

Initially, airway $CO_2$ dilution is applied to reach 25% of peak EAdi (in this case 30 µV). First level of flow may be calculated according to the respiratory drive of the patient and to parameters related to the patient. For example: Neural inspiratory time 1 sec. Predicted body weight is=70 kg. predicted tidal volume 70 kg×0.006 L/kg=0.42 L. Flow to be applied: 0.42 L/1 s×60=25 L/Min. Flow could then be increased in steps by a flow factor (e.g. 1.0 to 1.2 to 1.4 . . . ) until peak EAdi level of 30 µV has been reached, or until EAdi rise time has increased to its limit. Of course, a minimum and maximum flow limit and steps of increment could also be input manually.

Example of Airway $CO_2$ Dilution with Sub-Diaphragmatic Unloading and Negative End-Expiratory Pressure In the same or another non-limiting embodiment, once the airway $CO_2$ dilution reaches its targeted peak EAdi amplitude, sub-diaphragmatic unloading may be applied in several ways. For example, if a "fixed negative" pressure waveform is used for sub-diaphragmatic unloading, it could simply be applied in steps of e.g. −3 cm H2O until the 50% reduction in peak EAdi amplitude has been reached (i.e. 20 µV) or until the R-R interval limit has been reached. Another example describes delivering a "negative" pressure waveform "proportional" to the respiratory drive of the patient.

By calculating a gain (cm H2O/μV) predicting e.g. −5 cm H2O decrease in peak pressure at the current EAdi level of 30 μV (in this example −5 cm H2O/30 uV gives a gain of −0.17 cm H2O/μV). Based on reduction in EAdi (for example a reduction to 25 μV) a new gain will be calculated and applied (in this example −5 cm H2O/25 μV=0.2 cm H2O/μV). And so on until peak EAdi amplitude is less than −20 μV, where there has been a 50% reduction in neural respiratory drive with a 25% decrease in lung distending pressure and volume. Of course, a minimum and maximum gain limit and steps of its increment could also be input manually.

In one variant, negative end-expiratory pressure may be applied at a continuous fixed sub-diaphragmatic unloading negative pressure level.

In another variant of continuously proportional synchronized assist, negative end-expiratory pressure may indicate an increase of sub-diaphragmatic unloading. This means that reflexes regulating end-inspiratory and end-expiratory increasing lung volume are in full control of sub-diaphragmatic unloading. The pressure/gain steps of change may be input manually. If target reduction of Tonic EAdi has been achieved, the iteration may rest until Tonic EAdi exceeds upper limit where the iteration may restart. To avoid excessive application of negative end-expiratory pressure, a timer may be set to reduce negative end-expiratory pressure value by X % if less than upper Tonic EAdi limit for a given time period.

Example of airway $CO_2$ dilution with positive pressure assist and airway
$CO_2$ Dilution Airway PEEP In the same or another non-limiting embodiment, once the airway $CO_2$ dilution reached its peak EAdi limit, positive pressure assist and airway $CO_2$ dilution may also be applied in several ways. However, in contrast with sub-diaphragmatic unloading, positive pressure assist and airway $CO_2$ dilution require that airway $CO_2$ dilution delivers excessive flow during entire neural inspiration. This is because the positive pressure assist and airway $CO_2$ dilution controller uses this excessive flow that is leaving the airways to generate pressure between facial interface with valve (adjustable flow resistor) as well as in the airways. Given that flow of respiratory gas is controlled by the synchronized airway $CO_2$ dilution (AwCO$_2$Dil) sub-system 110, its "chemical" dilution effect will not be compromised.

Positive pressure assist and airway $CO_2$ dilution may either be applied for primary "mechanical" unloading or for a supplementary "mechanical" unloading if airway $CO_2$ dilution and sub-diaphragmatic unloading do not reach target suppression of neural respiratory drive (i.e. if EAdi is less than upper limit).

For example, positive pressure assist and airway $CO_2$ dilution may apply a "fixed positive" pressure waveform, simply being applied in steps of e.g. 3 cm H2O until the 50% reduction in peak EAdi amplitude has been reached (i.e. 20 μV) or until R-R interval limit has been reached. Positive pressure assist and airway $CO_2$ dilution may also deliver a "positive" pressure waveform "proportional" to the e.g. EAdi. A gain (cm H2O/μV) may be calculated, predicting e.g. 5 cm H2O decrease in peak pressure at the current EAdi level of 30 μV (in this example 5 cm H2O/30 uV gives a gain of 0.17 cm H2O/μV). Based on a reduction in EAdi (for example a reduction to 25 μV), a new gain may be calculated and applied (in this example 5 cm H2O/25 μV=0.2 cm H2O/μV). And so on, until the peak EAdi amplitude is less than 20 μV, where there has been a 50% reduction in neural respiratory drive with a 25% decrease in lung distending pressure and volume. Of course, a minimum and maximum gain limit and steps of its increment could also be input manually.

It may be observed that the application of airway $CO_2$ dilution with sub-diaphragmatic unloading and positive pressure assist and airway $CO_2$ dilution is dependent on age and underlying disorders. For example in infants, sub-diaphragmatic unloading could be the preferred first choice for "mechanical unloading" and could be supplemented by positive pressure assist and airway $CO_2$ dilution. In adults, positive pressure assist and airway $CO_2$ dilution preferred first choice for "mechanical unloading", but may be supplemented by sub-diaphragmatic unloading.

The fact that the peak EAdi has reached the upper peak EAdi limit does not reset the cycle of events. That is, if EAdi later goes above or below upper limits, either instantaneously or as calculated over a predetermined interval, the sequence of "chemical" reduction by AwCO$_2$dil in neural respiratory drive, lung distending pressures and tidal volume drive, and "mechanical" reduction in neural respiratory drive and respiratory work by sub-diaphragmatic unloading and/or positive Pressure Assist and airway $CO_2$ dilution (AwPass& $CO_2$dil), may start over from the new peak EAdi amplitude value.

Those of ordinary skill in the art will realize that the description of the systems, devices and methods for modulating a respiratory drive of a patient are illustrative only and are not intended to be in any way limiting. Other embodiments will readily suggest themselves to such persons with ordinary skill in the art having the benefit of the present disclosure. Furthermore, the disclosed systems, devices and methods may be customized to offer valuable solutions to existing needs and problems of conventional ventilatory assist technologies. In the interest of clarity, not all of the routine features of the implementations of the systems, devices and methods are shown and described. In particular, combinations of features are not limited to those presented in the foregoing description as combinations of elements listed in the appended claims form an integral part of the present disclosure. It will, of course, be appreciated that in the development of any such actual implementation of the systems, devices and methods, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of ventilatory assist technologies having the benefit of the present disclosure.

In accordance with the present disclosure, the sub-systems, components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer, a processor operatively connected to a memory, or a machine, those operations may be stored as a series of instructions readable by the machine, processor or computer, and may be stored on a non-transitory, tangible medium.

Systems and modules described herein may comprise software, firmware, hardware, or any combination(s) of software, firmware, or hardware suitable for the purposes described herein. Software and other modules may be executed by a processor and reside on a memory of servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A mechanical ventilation system for modulating a respiratory drive of a patient, comprising:
   a plurality of ventilation therapy sub-systems, including a synchronized airway $CO_2$ dilution ($AwCO_2Dil$) sub-system, wherein, each of the ventilation therapy sub-systems implement corresponding functions adapted to assist a corresponding reduction of the respiratory drive of the patient;
   a detector of the respiratory drive of the patient;
   an operator interface configured to receive one or more control parameters, the one or more control parameters include a maximum respiratory drive value and a respiratory drive rise time increase limit; and
   each of the therapeutic contributions represents a share of an excess of the respiratory drive of the patient above the maximum respiratory drive value to be controlled by a respective one of the plurality of ventilation therapy sub-systems; and
   a main controller operatively connected to each of the plurality of ventilation therapy sub-systems, to the detector of the respiratory drive of the patient and to the operator interface, the main controller being configured to:
   receive the one or more control parameters from the operator interface,
   receive measurements from the detector of the respiratory drive of the patient,
   assign, based on the respiratory drive of the patient and on the one or more control parameters, a therapeutic contribution to each of the plurality of ventilation therapy sub-systems for control of the respiratory drive of the patient, and
   control each of the plurality of the ventilation therapy sub-systems according to its assigned therapeutic contribution;
   the main controller being further configured to:
   detect, at each breath of the patient, a peak and a rise time of the respiratory drive of the patient; and
   implement a test stage comprising:
   causing a pause of at least one of the plurality of ventilation therapy sub-systems,
   comparing the rise time of the respiratory drive of the patient detected when the at least one of the plurality of ventilation therapy sub-systems is paused to the rise time of the respiratory drive of the patient detected when the at least one of the plurality of ventilation therapy sub-systems is not paused to detect an increase of the respiratory drive rise time of the patient, and
   ending the test stage after detecting the increase of the respiratory drive rise time.

2. The system of claim 1, wherein the main controller is configured to:
   compare a peak of the respiratory drive of the patient with the maximum respiratory drive value; and
   modify one of more of the therapeutic contributions if the peak of the respiratory drive of the patient exceeds the maximum respiratory drive value.

3. The system of claim 1, wherein the main controller is further adapted to:
   initiate a timer when the therapeutic contributions are assigned to each of the plurality of ventilation therapy sub-systems;
   upon expiry of the timer, compare a peak of the respiratory drive of the patient with the maximum respiratory drive value; and
   if the peak of the respiratory drive of the patient exceeds the maximum respiratory drive value upon expiry of the timer, cause the operator interface to display an alarm.

4. The system of claim 1, wherein:
   each of the therapeutic contributions to each of the plurality of ventilation therapy sub-systems is in a range of 0 to 100%; and
   a sum of all of the therapeutic contributions to each of the plurality of ventilation therapy sub-systems is equal to 100%.

5. The system of claim 1, wherein the one or more control parameters includes initial values for the therapeutic contributions.

6. The system of claim 5, wherein the initial value for the therapeutic contribution of one of the plurality of ventilation therapy sub-systems is 100% and the initial values for the therapeutic contributions of all other ones of the plurality of ventilation therapy sub-systems is 0%.

7. The system of claim 1, wherein the plurality of ventilation therapy sub-systems further comprise at least one ventilation therapy sub-system selected from:
   a synchronized sub-diaphragmatic unloading ($Di_{SUB}UL$) and sub-diaphragmatic negative end-expiratory pressure ($Di_{SUB}NEEP$) sub-system; and
   a synchronized positive pressure assist and airway $CO_2$ dilution ($AwPass\&CO_2Dil$) and airway positive end-expiratory pressure (AWPEEP) sub-system.

8. The system of claim 7, wherein the $AwCO_2Dil$ sub-system comprises:
   a non-pressurizing inspiratory flow delivery component adapted for being connected to airways of the patient and adapted to deliver a flow of respiratory gas toward the airways of the patient; and
   a first local controller operatively connected to the main controller and to the non-pressurizing inspiratory flow delivery component, the first local controller being adapted to:
   cause the non-pressurizing inspiratory flow delivery component to selectively deliver the flow of the respiratory gas toward the airways the patient, the flow being delivered at a multiple of a base flow at a start of an inspiratory phase of the patient and reducing to reach the base flow before an end of the inspiratory phase of the patient, the delivery of the respiratory gas selectively continuing at or below the base flow during an expiratory phase of the patient, and adjust the multiple of the base flow according to the respective therapeutic contribution for the AwCO$_2$Dil sub-system.

9. The system of claim 7, wherein the Di$_{SUB}$UL and Di$_{SUB}$NEEP sub-system comprises:

a diaphragm unloading component adapted for mounting on the abdomen of the patient and adapted to apply a negative pressure on the abdomen of the patient; and a second local controller operatively connected to the main controller and to the diaphragm unloading component, the second local controller being adapted to:

cause the diaphragm unloading component to selectively apply the negative pressure on the abdomen of the patient during the inspiratory phase of the patient, and adjust a level of the negative pressure on the abdomen of the patient according to the respective therapeutic contribution for the Di$_{SUB}$UL and Di$_{SUB}$NEEP sub-system.

10. The system of claim 8, wherein the AwPass&CO$_2$Dil and AWPEEP sub-system comprises:

the AwCO$_2$Dil sub-system; and a facial interface operatively connected to the first local controller and adapted for being connected to the airways of the patient and to induce a positive pressure in the airways of the patient;

wherein the first local controller is further adapted to cause the facial interface to selectively induce a positive pressure in the airways of the patient according to the respective therapeutic contribution for the AwPass&CO$_2$Dil and AWPEEP sub-system.

11. The system of claim 1, wherein the main controller is further adapted to control a loop comprising:

in a normal stage, causing the at least one of the plurality of ventilation therapy sub-systems to assist the corresponding reduction of the respiratory drive of the patient;

periodically interrupting the normal stage to execute the test stage; and after the test stage:

increasing a level of assistance of the at least one of the plurality of ventilation therapy sub-systems and returning to the normal stage if the peak of the respiratory drive of the patient is greater than the maximum respiratory drive value and the increase of the respiratory drive rise time is less than the respiratory drive rise time increase limit, decreasing the level of assistance of the at least one of the plurality of ventilation therapy sub-systems and returning to the normal stage if the peak of the respiratory drive of the patient is less than the maximum respiratory drive value, terminating the loop if the increase of the respiratory drive rise time exceeds the respiratory drive rise time increase limit, terminating the loop if the peak of the respiratory drive of the patient is in a range defined by the maximum respiratory drive value plus or minus a hysteresis value, and restarting the loop if the peak of the respiratory drive of the patient falls outside of the range defined by the maximum respiratory drive value plus or minus the hysteresis value.

12. A method for modulating a respiratory drive of a patient, comprising:

receiving one or more control parameters from an operator interface including a maximum respiratory drive value and a respiratory drive rise time increase limit;

detecting the respiratory drive of the patient;

assign, based on the respiratory drive of the patient and on the one or more control parameters, a therapeutic contribution to each of a plurality of ventilation therapy sub-systems, including a synchronized airway CO$_2$ dilution (AwCO$_2$Dil) subsystem, each of the ventilation therapy sub-systems implementing corresponding functions adapted to assist a corresponding reduction of the respiratory drive of the patient;

each of the therapeutic contributions represents a share of an excess of the respiratory drive of the patient above the maximum respiratory drive value to be controlled by a respective one of the plurality of ventilation therapy sub-systems; and controlling each of the plurality of the ventilation therapy sub-systems according to its assigned therapeutic contribution;

detecting, at each breath of the patient, a peak and a rise time of the respiratory drive of the patient; and implementing a test stage comprising:

causing a pause of at least one of the plurality of ventilation therapy sub-systems, comparing the rise time of the respiratory drive of the patient detected when the at least one of the plurality of ventilation therapy sub-systems is paused to the rise time of the respiratory drive of the patient detected when the at least one of the plurality of ventilation therapy sub-systems is not paused to detect an increase of the respiratory drive rise time of the patient, and ending the test stage after detecting the increase of the respiratory drive rise time.

13. The method of claim 12, further comprising:

initiating a timer when the therapeutic contributions are assigned to each of the plurality of ventilation therapy sub-systems;

upon expiry of the timer, comparing a peak of the respiratory drive of the patient with the maximum respiratory drive value; and modifying one or more of the therapeutic contributions if the peak of the respiratory drive of the patient exceeds the maximum respiratory drive value upon expiry of the timer.

14. The method of claim 13, further comprising:

selectively applying a negative pressure on the abdomen of the patient during an inspiratory phase of the patient; and adjusting a level of the negative pressure on the abdomen of the patient according to a respective therapeutic contribution for a third one of the plurality of ventilation therapy sub-systems.

15. The method of claim 12, further comprising:

using a non-pressurizing inspiratory flow delivery component adapted for being connected to airways of the patient to selectively deliver a flow of respiratory gas toward the airways the patient, the flow being delivered at a multiple of a base flow at a start of an inspiratory phase of the patient and being reduced to reach the base flow before an end of the inspiratory phase of the patient, the delivery of the respiratory gas selectively continuing at or below the base flow during an expiratory phase of the patient; and adjusting the multiple of the base flow according to a respective therapeutic contribution for a first one of the plurality of ventilation therapy sub-systems.

16. The method of claim 15, further comprising selectively inducing a positive pressure in the airways of the patient, a level of the positive pressure being adjusted according to a respective therapeutic contribution for a second one of the plurality of ventilation therapy sub-systems.

17. A mechanical ventilation system for modulating a respiratory drive of a patient, comprising:
a plurality of ventilation therapy sub-systems, including a synchronized airway $CO_2$ dilution ($AwCO_2Dil$) sub-system, wherein, each of the ventilation therapy sub-systems implement corresponding functions adapted to assist a corresponding reduction of the respiratory drive of the patient;
a detector of the respiratory drive of the patient;
an operator interface configured to receive one or more control parameters, the one or more control parameters include a maximum respiratory drive value and a heart rate increase limit; and
each of the therapeutic contributions represents a share of an excess of the respiratory drive of the patient above the maximum respiratory drive value to be controlled by a respective one of the plurality of ventilation therapy sub-systems; and
a main controller operatively connected to each of the plurality of ventilation therapy sub-systems, to the detector of the respiratory drive of the patient and to the operator interface, the main controller being configured to:
receive the one or more control parameters from the operator interface,
receive measurements from the detector of the respiratory drive of the patient,
assign, based on the respiratory drive of the patient and on the one or more control parameters, a therapeutic contribution to each of the plurality of ventilation therapy sub-systems for control of the respiratory drive of the patient, and
control each of the plurality of the ventilation therapy sub-systems according to its assigned therapeutic contribution;
the main controller being further configured to:
detect, at each breath of the patient, a heart rate and a peak of the respiratory drive of the patient; and
implement a test stage comprising:
causing a pause of at least one of the plurality of ventilation therapy sub-systems,
comparing the heart rate of the patient when the at least one of the plurality of ventilation therapy sub-systems is paused to the heart rate of the patient when the at least one of the plurality of ventilation therapy sub-systems is not paused to calculate an increase of the heart rate; and
ending the test stage after calculating the increase of the heart rate.

18. The system of claim 17, wherein the main controller is further adapted to control a loop comprising:
in a normal stage, causing the at least one of the plurality of ventilation therapy sub-systems to assist the corresponding reduction of the respiratory drive of the patient;
periodically interrupting the normal stage to execute the test stage; and
after the test stage:
increasing a level of assistance of the at least one of the plurality of ventilation therapy sub-systems and returning to the normal stage if the peak of the respiratory drive of the patient is greater than the maximum respiratory drive value and the increase of the heart rate is less than the heart rate increase limit,
decreasing the level of assistance of the at least one of the plurality of ventilation therapy sub-systems and returning to the normal stage if the peak of the respiratory drive of the patient is less than the maximum respiratory drive value,
terminating the loop if the increase of the heart rate is greater than the heart rate increase limit, and
terminating the loop if the peak of the respiratory drive of the patient is in a range defined by the maximum respiratory drive value plus or minus a hysteresis value, and
restarting the loop if the peak of the respiratory drive of the patient falls outside of the range defined by the maximum respiratory drive value plus or minus the hysteresis value.

* * * * *